United States Patent [19]

Dower et al.

[11] Patent Number: 5,432,018
[45] Date of Patent: Jul. 11, 1995

[54] PEPTIDE LIBRARY AND SCREENING SYSTEMS

[75] Inventors: William J. Dower, Menlo Park; Steven E. Cwirla, Palo Alto; Ronald W. Barrett, Sunnyvale, all of Calif.

[73] Assignee: Affymax Technologies N.V., Netherlands

[21] Appl. No.: 718,577

[22] Filed: Jun. 20, 1991

Related U.S. Application Data

[63] Continuation-in-part of Ser. No. 541,108, Jun. 20, 1990.

[51] Int. Cl.$^6$ .............................................. C12Q 1/70
[52] U.S. Cl. .................................... 435/5; 435/69.1; 435/172.3; 435/235.1; 935/80; 935/81
[58] Field of Search ............... 435/5, 69.1, 172.3, 435/235.1; 935/80, 81

[56] References Cited

U.S. PATENT DOCUMENTS

| | | | |
|---|---|---|---|
| 4,359,535 | 11/1982 | Pieczenik | 435/317 |
| 4,593,002 | 6/1986 | Dulbecco | 435/172.3 |
| 4,910,140 | 3/1990 | Dower | 435/172.2 |
| 5,223,409 | 6/1993 | Ladner et al. | 435/69.7 |

FOREIGN PATENT DOCUMENTS

| | | |
|---|---|---|
| 2183661 | 10/1986 | United Kingdom . |
| 8701374 | 3/1987 | WIPO . |
| 8805085 | 7/1988 | WIPO . |
| 8806630 | 9/1988 | WIPO . |
| 8906694 | 7/1989 | WIPO . |
| 9002809 | 3/1990 | WIPO . |
| 9005144 | 5/1990 | WIPO . |
| 9014424 | 11/1990 | WIPO . |
| 9118980 | 12/1991 | WIPO . |
| 9201047 | 1/1992 | WIPO . |
| 9207077 | 4/1992 | WIPO . |
| 9209690 | 6/1992 | WIPO . |
| 9215677 | 9/1992 | WIPO . |
| 9215679 | 9/1992 | WIPO . |

OTHER PUBLICATIONS

Ward et al., Binding activites of a repertoire of single Immunoglobulin variable domains secreted from *Escherichia coli*, Nature 341:544–548, 1989.
McCafferty et al., Nature 348:522–554, 1990.
Scott and Smith, Science 249:386–390, 1990.
Cwirla et al., Proc. Natl Acad Sci. 87:6378–6382, 1990.
Oliphant et al., Gene 177–183, 1986.
Parmley et al., Gene 73:305–318, 1988.
Greenwood et al., 1991, J. Mol. Biol. 220:821–827.
Felici et al., 1991, J. Mol. Biol. 222:301–310.
Garrard et al., Dec. 1991, Bio/Technology 9:1373–1377.
Parmley and Smith, 1989, Adv. Exp. Med. Biol. 251:215–218.
De la Cruz et al., 25 Mar. 1988, J. Biol. Chem. 263(9):4318–4322.
Il'ichev et al., Mar.-Apr. 1990, Molekulyarnaya Biologiya 24(2):530–535 (English translation).
Barrett et al., 1992, Analyt. Biochem. 204:357–364.
Bass et al., 1990, Proteins: Structure, Functions and Genetics 8:309–314.
PCT Patent Publication No. 90/14443 to Huse, Nov. 1990.
Devlin et al., 27 Jul. 1990, Science 249:404–406.
Smith et al., 1990, J. Cell. Biochem. Supp. 14C:246, abst. CK319 (19th Ann. Mtg., UCLA Symp. Mol. Cell. Biol., 3 Feb. to 11 Mar. 1990).

(List continued on next page.)

*Primary Examiner*—Toni R. Scheiner
*Assistant Examiner*—Donna C. Wortman
*Attorney, Agent, or Firm*—Townsend and Townsend Khourie and Crew

[57] ABSTRACT

Peptides which bind to selected receptors are identified by screening libraries which encode a random or controlled collection of amino acids. Peptides encoded by the libraries are expressed as fusion proteins of bacteriophage coat proteins, and bacteriophage are then screened against the receptors of interest. Peptides having a wide variety of uses, such as therapeutic or diagnostic reagents, may thus be identified without any prior information on the structure of the expected ligand or receptor.

12 Claims, 7 Drawing Sheets

OTHER PUBLICATIONS

Scott et al., 1990, Advances in Gene Technology: The Molecular Biology of Immune Diseases and the Immune Resonse (Streilein et al., eds., IRL Press, Oxford), p. 224.

Huse et al., 8 Dec. 1989, Science 246:1275–1281.

Ward et al., 12 Oct. 1989, Nature 341:544–545.

Better et al., 20 May 1988, Science 240:1041–1043.

Skerra and Pluckthun, 20 May 1988, Scinece 240:1038–1041.

Dower et al., 1988, Nucl. Acids Res. 16(13):6127–6145.

Geysen et al., 1987, J. Immunol. Meth. 102:259–274.

Aruffo and Seed, 1987, Proc. Natl. Acad. Sci. USA 84:8573–8577.

Smith, 14 Jun. 1985, Science 228:1315–1317.

Young and Davis, 18 Nov. 1983, Science 222:778–782.

Boeke and Model, Sep. 1982, Proc. Natl. Acad. Sci. USA 79:5200–5204.

Zacher et al., 1980, Gene 9:127–140.

Goldsmith and Konigsberg, 1977, Biochem. 16(12):2686–2694.

Hoogenboom et al., 1991 Nuc. Acids Res. 19(15):4133–4137.

Barbas III et al., Sep. 1991, Proc. Natl. Acad. Sci. USA 88:7978–7982.

Kang et al., May 1991, Proc. Natl. Acad. Sci. USA 88:4363–4366.

| | | | | |
|---|---|---|---|---|
| YGGLGL | YGSLVL | YGALGG | YGWWGL | YGLWQS |
| YGGLGI | YGSLVQ | YGALSW | YGWWLT | YGFWGM |
| YGGLGR | YGSLVR | YGALDT | YGWLAT | YGKWSG |
| YGGLNV | YGSLAD | YGALEL | YGWANK | YGPFWS |
| YGGLRA | YGSLLS | | | YGEFVL |
| YGGLEM | YGSLNG | YGAIGF | YGNWTY | YGDFAF |
| | YGSLYE | | YGNFAD | |
| YGGIAS | | YGAWTR | YGNFPA | YAWGWG |
| YGGIAV | | | | YAGFAQ |
| YGGIRP | YGSWAS | | YGTFIL | |
| YGGIRP | YGSWAS | | YGTWST | YSMFKE |
| | YGSWQA | | | |
| YGGWAG | YGSFLH | | YGVWAS | |
| YGGWGP | | | YGVWWR | |
| YGGWSS | | | | |
| YGGMKV | | | | |
| YGGFPD | | | | |

*FIG. 4.*

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
      ( A ) LENGTH: 5 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

Tyr  Gly  Gly  Phe  Leu
   1                     5

( 2 ) INFORMATION FOR SEQ ID NO:2:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

Tyr  Gly  Phe  Trp  Gly  Met
   1                     5

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:3:

Tyr Ala Gly Phe Ala Gln
1               5

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Tyr Gly Ala Phe Gln Gly
1               5

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Tyr Gly Gly Phe Leu Thr
1               5

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Tyr Gly Tyr Trp Ser Leu
1               5

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Tyr Gly Ala Phe Met Gln
1               5

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Tyr Gly Ala Phe Phe Gln
1               5

( 2 ) INFORMATION FOR SEQ ID NO:9:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Tyr Gly Ala Phe Phe Lys
1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Tyr Gly Phe Trp Ser Asn
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Tyr Gly Ala Phe Gly Gly
1               5

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Tyr Gly Gly Phe Gly Phe
1               5

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Tyr Gly Val Phe Ser Arg
1               5

( 2 ) INFORMATION FOR SEQ ID NO:14:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Tyr  Gly  Gly  Leu  Ser  Met
 1                    5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Tyr  Gly  Thr  Phe  Leu  Asn
 1                    5
```

( 2 ) INFORMATION FOR SEQ ID NO:16:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Tyr  Gly  Gly  Leu  Val  Arg
 1                    5
```

( 2 ) INFORMATION FOR SEQ ID NO:17:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Tyr  Gly  Ser  Phe  Ser  Leu
 1                    5
```

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
Tyr  Gly  Ala  Trp  Tyr  Thr
 1                    5
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Tyr  Gly  Arg  Phe  Phe  His
    1                       5

(2) INFORMATION FOR SEQ ID NO:20:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

Tyr  Gly  Gly  Leu  Arg  His
    1                       5

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

Tyr  Gly  Ser  Phe  Met  Ala
    1                       5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

Tyr  Gly  Gly  Phe  Ser  Pro
    1                       5

PEPTIDE LIBRARY AND SCREENING SYSTEMS

RELATED APPLICATIONS

This application is a continuation-in-part of Ser. No. 07/541,108, filed Jun. 20, 1990.

FIELD OF THE INVENTION

The present invention relates generally to methods for selecting peptide ligands to receptor molecules of interest and, more particularly, to methods for generating and screening large peptide libraries for peptides with desired binding characteristics.

BACKGROUND OF THE INVENTION

As molecular biology has helped to define regions of proteins that contribute to a particular biological activity, it has become desirable to synthesize short peptides to mimic (or inhibit) those activities. Many of the disadvantages encountered in therapeutic, diagnostic and industrial settings with purified proteins, or those produced by recombinant means, could easily be avoided by short synthetic peptides. For instance, synthetic peptides offer advantages of specificity, convenience of sample or bulk preparation, lower relative cost, high degree of purity, and long shelf-life.

Despite the great promise of synthetic peptides, the technology remains, to a large extent, a laboratory tool. Precise sequence and binding data are not available for most proteins of significant medical, agricultural or industrial interest. Even when the sequence of a protein is known, the process of identifying short sequences which are responsible for or contribute to a biological activity may be extremely tedious, if not nearly impossible in many instances.

Thus, the ability to generate and efficiently screen very large collections of peptides for desired binding activities would be of enormous interest. It would enable the identification of novel agonists and antagonists for receptors, the isolation of specific inhibitors of enzymes, provide probes for structural and functional analyses of binding sites of many proteins, and ligands for many other compounds employed in a wide variety of applications.

The generation of large numbers of peptide sequences by the cloning and expression of randomly-generated mixtures of oligonucleotides is possible in the appropriate recombinant vectors. See, e.g., Oliphant et al., *Gene* 44:177–183 (1986). Such a large number of compounds can be produced, however, that methods for efficient physical and genetic selection are required. Without such methods the usefulness of these large peptide libraries in providing ligands of potential interest may be lost. The present invention provides methods for efficient screening and selection from a large peptide library, fulfilling these and other related needs.

SUMMARY OF THE INVENTION

The present invention provides novel methods and compositions for identifying peptides which bind to preselected receptor molecules. The peptides find a variety of therapeutic, diagnostic and related uses, e.g., to bind the receptor or an analogue thereof and inhibit or promote its activity.

In one embodiment the invention relates to methods for identifying the peptides which bind to a preselected receptor. In certain aspects the methods generally comprise constructing a bacteriophage expression vector which comprises an oligonucleotide library of at least about $10^6$ members which encode the peptides. The library member is joined in reading frame to the 5' region of a nucleotide sequence encoding an outer structural protein of the bacteriophage. Appropriate host cells are transformed with the expression vectors, generally by electroporation, and the transformed cells cultivated under conditions suitable for expression and assembly of bacteriophage. Using an affinity screening process, bacteriophage library members are contacted with the preselected receptor under conditions conducive to specific peptide-receptor binding, and bacteriophage whose coat proteins have peptides which bind the receptor molecule are selected. The nucleotide sequence which encodes the peptide on the selected phage may then be determined. By repeating the affinity selection process one or more times, the peptides of interest may be enriched. By increasing the stringency of the selection, e.g., by reducing the valency of the peptide-phage interaction towards substantial monovalency, peptides of increasingly higher affinity can be identified.

In another aspect the methods are concerned with expression vectors having the oligonucleotide library members joined in reading frame with a nucleotide sequence to encode a fusion protein, wherein the library member represents the 5' member of the fusion and the 3' member comprises at least a portion of an outer structural protein of the bacteriophage. The first residue of the peptide encoded by the library member may be at the 5'-terminus of the sequence encoding the phage coat protein. In preferred embodiments, where phage proteins are initially expressed as preproteins and then processed by the host cell to a mature protein, the library members are inserted so as to leave the peptide encoded thereby at the N-terminus of the mature phage protein after processing or a protein substantially homologous thereto.

The invention also concerns host cells transformed with a bacteriophage expression vector having an oligonucleotide library member, joined in reading frame to the 5' region of a nucleotide sequence encoding an outer structural protein of the bacteriophage, wherein the library member encodes a peptide of at least about five to twenty-five amino acids.

Generally, the oligonucleotide library of the invention comprises a variable codon region which encodes for the peptides of interest, and may optionally comprise sequences coding for one or more spacer amino acid residues, such as Gly. The variable region may be encoded by $(NNK)_x$ or $(NNS)_x$, where N is A, C, G or T, K is G or T, S is G or C, and x is from 5 to at least about 8. In certain preferred embodiments the variable region of the oligonucleotide library member encodes a hexapeptide. The variable codon region may also be prepared from a condensation of activated trinucleotides.

BRIEF DESCRIPTION OF THE DRAWINGS

FIG. 1 depicts the construction of an oligonucleotide library. (A) The vector fAFF1 contains two non-complementary BstXI sites separated by a 30 bp stuffer fragment. Removal of the BstXI fragment allows oriented ligation of oligonucleotides with the appropriate cohesive ends. (B) The oligonucleotide ON-49 was annealed to two "half-site" fragments to form cohesive termini complementary to BstXI sites 1 and 2 in the vector. The gapped structure, where the single-stranded region comprises the variable hexacodon sequence and a 2 (gly) codon spacer, was ligated to the vector and electro-transformed into E. coli.

FIG. 2 depicts the amino acid sequences (deduced from DNA sequence) of the N-terminal hexapeptides on pIII of infectious phage randomly selected from the library. Sequences begin at the signal peptidase site. Single letter code for amino acids is A (Ala), C (Cys), D (Asp), E (Glu), F (Phe), G (Gly), H (His), I (Ile), K (Lys), L (Leu), M (Met), N (Asn), P (Pro), Q (Gln), R (Arg), S (Ser), T (Thr), V (Val), W (Trp), Y (Tyr).

FIG. 4 shows the amino acid sequences (deduced from DNA sequence) of the N-terminal peptides of pIII of 52 phage isolated by three rounds of panning on mAB 3E7.

DESCRIPTION OF THE SPECIFIC EMBODIMENTS

Figure 3:
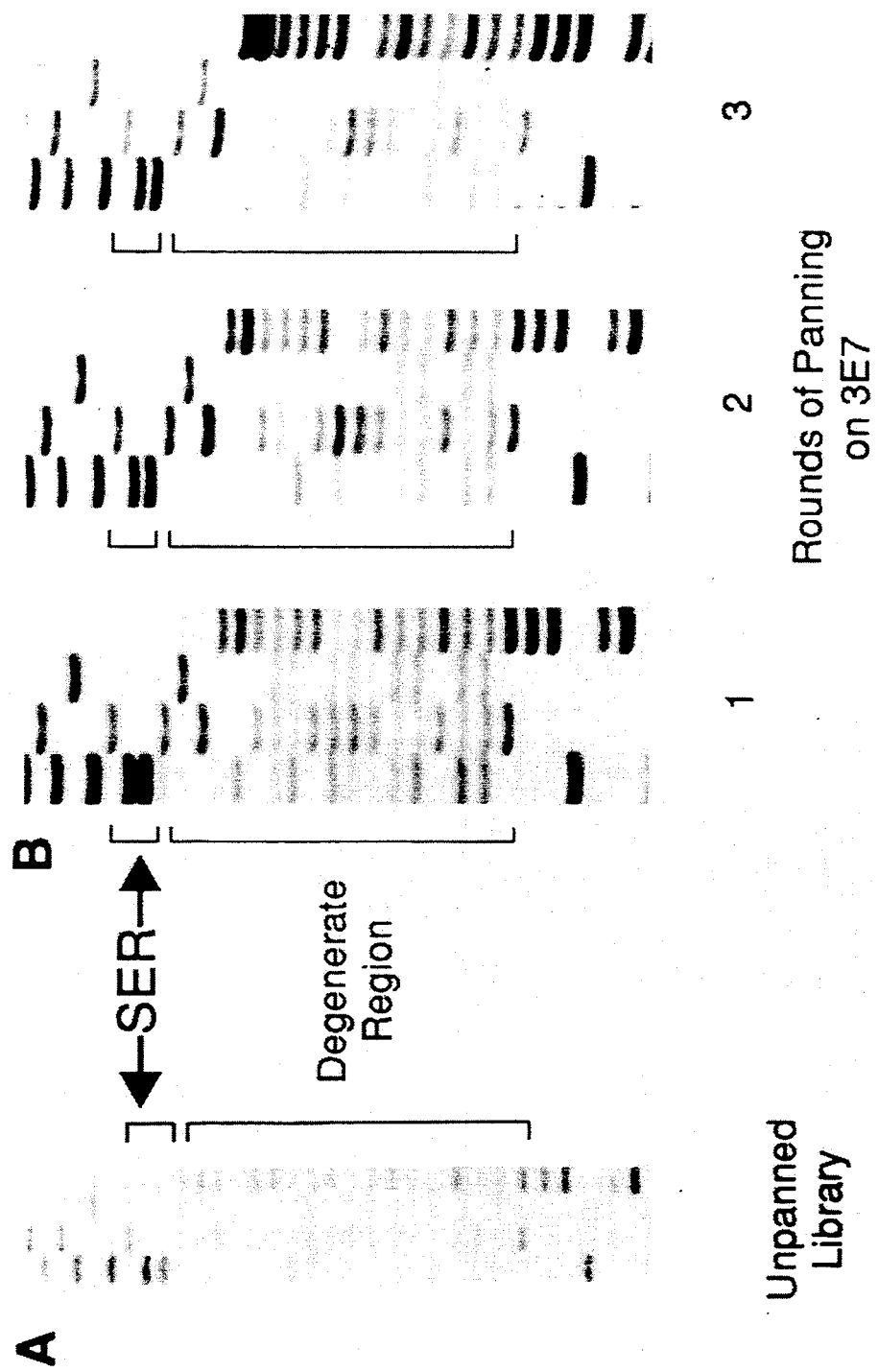
FIG. 3 illustrates the composite DNA sequence of the variable region of pools of (A) infectious phage from the library, and (B) phage recovered from 1, 2, or 3 rounds of panning on mAB 3E7. Phage were amplified as tetracycline resistant colonies and DNA from a pool of phage derived from several thousand of these colonies was isolated and sequenced. The area of the sequencing gel corresponding to the cloning site in geneIII is displayed. A sequencing primer was annealed to the phage DNA ~40 bases to the 3' side of the cloning site. The actual readout of the gel is the sequence complementary to the coding strand. For clarity of codon identification, the lanes may be read as C, T, A, G, left to right and 5' to 3', top to bottom, to identify the sequence of the coding (+) strand.

Methods and compositions are provided for identifying peptides which bind to receptor molecules of interest. The peptides are produced from oligonucleotide libraries which encode peptides attached to a bacteriophage structural protein. A method of affinity enrichment allows a very large library of peptides to be screened and the phage carrying the desired peptide(s) selected. The nucleic acid may then be isolated from the phage and the variable region of the oligonucleotide library member sequenced, such that the amino acid sequence of the desired peptide is deduced therefrom. Using these methods a peptide identified as having a binding affinity for the desired molecule may then be synthesized in bulk by conventional means.

By identifying the peptide de novo one need not know the sequence or structure of the receptor molecule or the sequence of its natural binding partner. Indeed, for many "receptor" molecules a binding partner has not yet been identified. A significant advantage of the present invention is that no prior information regarding an expected ligand structure is required to isolate peptide ligands of interest. The peptide identified will thus have biological activity, which is meant to include at least specific binding affinity for a selected receptor molecule, and in some instances will further include the ability to block the binding of other compounds, to stimulate or inhibit metabolic pathways, to act as a signal or messenger, to stimulate or inhibit cellular activity, and the like.

The number of possible receptor molecules for which peptide ligands may be identified by means of the present invention is virtually unlimited. For example, the receptor molecule may be an antibody (or a binding portion thereof). The antigen to which the antibody binds may be known and perhaps even sequenced, in which case the invention may be used to map epitopes of the antigen. If the antigen is unknown, such as with certain autoimmune diseases, for example, sera or other fluids from patients with the disease can be used in the present methods to identify peptides, and consequently the antigen which elicits the autoimmune response. It is also possible using these methods to tailor a peptide to fit a particular individual's disease. Once a peptide has been identified it may itself serve as, or provide the basis for, the development of a vaccine, a therapeutic agent, a diagnostic reagent, etc.

The present invention can identify peptide ligands for a wide variety of substances in addition to antibodies. These include, by way of example and not limitation, growth factors, hormones, enzymes, interferons, interleukins, intracellular and intercellular messengers, lectins, cellular adhesion molecules and the like, as well as the ligands for the corresponding receptors of the aforementioned molecules. It will be recognized that peptide ligands may also be identified by the present invention for molecules which are not peptides or proteins, e.g., carbohydrates, non-protein organic compounds, metals, etc. Thus, although antibodies are widely available and conveniently manipulated, they are merely representative of receptor molecules for which peptide ligands can be identified by means of the present invention.

An oligonucleotide library, prepared according to the criteria as described herein, is inserted in an appropriate vector encoding a bacteriophage structural protein, preferably an accessible phage protein, such as a bacteriophage coat protein. Although one skilled in the art will appreciate that a variety of bacteriophage may be employed in the present invention, in preferred embodiments the vector is, or is derived from, a filamentous bacteriophage, such as, for example, f1, fd, Pf1, M13, etc. In a more preferred embodiment the filamentous phage is fd, and contains a selectable marker such as tetracycline (e.g., "fd-tet"). The fd-tet vector has been extensively described in the literature. See, for example, Zacher et al., Gene 9:127–140 (1980), Smith et al., Science 228:1315–1317 (1985) and Parmley and Smith, Gene 73:305–318 (1988), each incorporated by reference herein.

The phage vector is chosen to contain or is constructed to contain a cloning site located in the 5' region of the gene encoding the bacteriophage structural protein, so that the peptide is accessible to receptors in an affinity selection and enrichment procedure as described below. As the structural phage protein is preferably a coat protein, in phage fd the preferred coat protein is pIII. Each filamentous fd phage is known to have up to four or five copies of the pIII protein.

An appropriate vector allows oriented cloning of the oligonucleotide sequences which encode the peptide so that the peptide is expressed at or within a distance of about 100 amino acid residues of the N-terminus of the mature coat protein. The coat protein is typically expressed as a preprotein, having a leader sequence. Thus, desirably the oligonucleotide library is inserted so that the N-terminus of the processed bacteriophage outer protein is the first residue of the peptide, i.e., between the 3'-terminus of the sequence encoding the leader protein and the 5-terminus of the sequence encoding the mature protein or a portion of the 5' terminus.

The library is constructed by cloning an oligonucleotide which contains the variable region of library members (and any spacers, framework determinants, etc. as discussed below) into the selected cloning site. Using known recombinant DNA techniques (see generally, Sambrook et al., *Molecular Cloning, A Laboratory Manual*, 2d ed., Cold Spring Harbor Laboratory Press, Cold Spring Harbor, N.Y., 1989, incorporated by reference herein), an oligonucleotide may be constructed which, inter alia, removes unwanted restriction sites and adds desired ones, reconstructs the correct portions of any sequences which have been removed (such as a correct signal peptidase site, for example), inserts the spacer conserved or framework residues, if any, and corrects the translation frame (if necessary) to produce active, infective phage. The central portion of the oligonucleotide will generally contain one or more of the variable region domain(s) and the spacer or framework residues. The sequences are ultimately expressed as peptides (with or without spacer or framework residues) fused to or in the N-terminus of the mature coat protein on the outer, accessible surface of the assembled bacteriophage particles.

The variable region domain of the oligonucleotide comprises the source of the library. The size of the library will vary according to the number of variable codons, and hence the size of the peptides, which are desired. Generally the library will be at least about $10^6$ members, usually at least $10^7$ and typically $10^8$ or more members. To generate the collection of oligonucleotides which forms a series of codons encoding a random collection of amino acids and which is ultimately cloned into the vector, a codon motif is used, such as $(NNK)_x$, where N may be A, C, G, or T (nominally equimolar), K is G or T (nominally equimolar), and x is typically up to about 5, 6, 7, or 8 or more, thereby producing libraries of penta-, hexa-, hepta-, and octa-peptides or more. The third position may also be G or C, designated "S". Thus, NNK or NNS (i) code for all the amino acids, (ii) code for only one stop codon, and (iii) reduce the range of codon bias from 6:1 to 3:1. It should be understood that with longer peptides the size of the library which is generated may become a constraint in the cloning process and thus the larger libraries can be sampled, as described hereinbelow. The expression of peptides from randomly generated mixtures of oligonucleotides in appropriate recombinant vectors is discussed in Oliphant et al., *Gene* 44:177–183 (1986), incorporated herein by reference.

An exemplified codon motif $(NNK)_6$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with only three-codon amino acids.

An alternative approach to minimize the bias against one-codon residues involves the synthesis of 20 activated tri-nucleotides, each representing the codon for one of the 20 genetically encoded amino acids. These are synthesized by conventional means, removed from the support but maintaining the base and 5-HO-protecting groups, and activated by the addition of 3'O-phosphoramidite (and phosphate protection with beta cyanoethyl groups) by the method used for the activation of mononucleosides, as generally described in McBride and Caruthers, *Tetrahedron Letters* 22:245 (1983), which is incorporated by reference herein. Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis*, M. J. Gait, ed. p35–82 (1984). Thus, this procedure generates a population of oligonucleotides for cloning that is capable of encoding an equal distribution (or a controlled unequal distribution) of the possible peptide sequences. This approach may be especially useful in generating longer peptide sequences, since the range of bias produced by the $(NNK)_6$ motif increases by three-fold with each additional amino acid residue.

When the codon motif is $(NNK)_x$, as defined above, and when x equals 8, there are $2.6 \times 10^{10}$ possible octapeptides. A library containing most of the octa-peptides may be difficult to produce. Thus, a sampling of the octa-peptides may be accomplished by constructing a subset library using of about 0.1%, and up to as much as 1%, 5% or 10% of the possible sequences, which subset of recombinant bacteriophage particles is then screened. As the library size increases, smaller percentages are acceptable. If desired, to extend the diversity of a subset library the recovered phage subset may be subjected to mutagenesis and then subjected to subsequent rounds of screening. This mutagenesis step may be accomplished in two general ways: the variable region of the recovered phage may be mutagenized, or additional variable amino acids may be added to the regions adjoining the initial variable sequences.

A variety of techniques can be used in the present invention to diversify a peptide library or to diversify around peptides found in early rounds of panning to have sufficient binding activity. In one approach, the positive phage (those identified in an early round of panning) are sequenced to determine the identity of the active peptides. Oligonucleotides are then synthesized based on these peptide sequences, employing a low level of all bases incorporated at each step to produce slight variations of the primary oligonucleotide sequences. This mixture of (slightly) degenerate oligonucleotides is then cloned into the affinity phage as described herein. This method produces systematic, controlled variations of the starting peptide sequences. It requires, however, that individual positive phage be sequenced before mutagenesis, and thus is useful for expanding the diversity of small numbers of recovered phage.

Another technique for diversifying around the recognition kernel of the selected phage-peptide involves the subtle misincorporation of nucleotide changes in the peptide through the use of the polymerase chain reaction (PCR) under low fidelity conditions. A protocol of Leung at al., *Technique* 1:11-15 (1989) alters the ratios of nucleotides and the addition of manganese ions to produce a 2% mutation frequency. Yet another approach for diversifying the selected phage involves the mutagenesis of a pool, or subset, of recovered phage. Phage recovered from panning are pooled and single stranded DNA is isolated. The DNA is mutagenized by treatment with, e.g., nitrous acid, formic acid, or hydrazine. These treatments produce a variety of damage in the DNA. The damaged DNA is then copied with reverse transcriptase which misincorporates bases when it encounters a site of damage. The segment containing the sequence encoding the variable peptide is then isolated by cutting with restriction nuclease(s) specific for sites flanking the variable region. This mutagenized segment is then recloned into undamaged vector DNA in a manner similar to that described herein. The DNA is transformed into cells and a secondary library is constructed as described. The general mutagenesis method is described in detail in Myers, et al., *Nucl. Acids Res.* 13:3131-3145 (1985), Myers et al., *Science* 229:242-246 (1985), and Myers, *Current Protocols in Molecular Biology* Vol I, 8.3.1-8.3.6, F. Ausebel, et al., eds, J. Wiley and Sons, New York (1989), each of which are incorporated herein by reference.

In the second general approach, that of adding additional amino acids to a peptide or peptides found to be active, a variety of methods are available. In one, the sequences of peptides selected in early panning are determined individually and new oligonucleotides, incorporating the determined sequence and an adjoining degenerate sequence, are synthesized. These are then cloned to produce a secondary library.

In another approach which adds a second variable region to a pool of peptide-bearing phage, a restriction site is installed next to the primary variable region. Preferably, the enzyme should cut outside of its recognition sequence, such as BspMI which cuts leaving a four base 5' overhang, four bases to the 3' side of the recognition site. Thus, the recognition site may be placed four bases from the primary degenerate region. To insert a second variable region, the pool of phage DNA is digested and blunt-ended by filling in the overhang with Klenow fragment. Double-stranded, blunt-ended, degenerately synthesized oligonucleotides are then ligated into this site to produce a second variable region juxtaposed to the primary variable region. This secondary library is then amplified and screened as before.

While in some instances it may be appropriate to synthesize peptides having contiguous variable regions to bind certain receptors, in other cases it may be desirable to provide peptides having two or more regions of diversity separated by spacer residues. For example, the variable regions may be separated by spacers which allow the diversity domains of the peptides to be presented to the receptor in different ways. The distance between variable regions may be as little as one residue, sometimes five to ten and up to about 100 residues. For probing a large binding site the variable regions may be separated by a spacer of residues of 20 to 30 amino acids. The number of spacer residues when present will preferably be at least two, typically at least three or more, and often will be less than ten, more often less than eight residues.

Thus, an oligonucleotide library having variable domains separated by spacers can be represented by the formula:

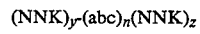

$$(NNK)_y\text{-}(abc)_n(NNK)_z$$

where N and K are as defined previously (note that S as defined previously may be substituted for K), and y+z is equal to about 5, 6, 7, 8, or more, a, b and c represent the same or different nucleotides comprising a codon encoding spacer amino acids, n is up to about 20 to 30 amino acids or more.

The spacer residues may be somewhat flexible, comprising oligo-glycine, for example, to provide the diversity domains of the library with the ability to interact with sites in a large binding site relatively unconstrained by attachment to the phage protein. Rigid spacers, such as, e.g., oligo-proline, may also be inserted separately or in combination with other spacers, including Gly. It may be desired to have the variable domains close to one another and use a spacer to orient the variable domain with respect to each other, such as by employing a turn between the two sequences as might be provided by a spacer of the sequence Gly-Pro-Gly, for example. To add stability to such a turn, it may be desirable or necessary to add Cys residues at either or both ends of each variable region. The Cys residues would then form disulfide bridges to hold the variable regions together in a loop, and in this fashion may also serve to mimic a cyclic peptide. Of course, those skilled in the art will appreciate that various other types of covalent linkages for cyclization may also be accomplished.

The spacer residues described above can also be situated on either or both ends of the variable nucleotide region. For instance, a cyclic peptide may be accomplished without an intervening spacer, by having a Cys residue on both ends of the peptide. As above, flexible spacers, e.g., oligo-glycine, may facilitate interaction of the peptide with the selected receptors. Alternatively, rigid spacers may allow the peptide to be presented as if on the end of a rigid arm, where the number of residues, e.g., Pro, determines not only the length of the arm but also the direction for the arm in which the peptide is oriented. Hydrophilic spacers, made up of charged and/or uncharged hydrophilic amino acids, (e.g., Thr, His, Asn, Gln, Arg, Glu, Asp, Met, Lys, etc.), or hydrophobic spacers of hydrophobic amino acids (e.g., Phe, Leu, Ile, Gly, Val, Ala, etc.) may be used to present the peptides to binding sites with a variety of local environments.

Unless modified during or after synthesis by the translation machinery, recombinant peptide libraries consist of sequences of the 20 normal L-amino acids. While the available structural diversity for such a library is large, additional diversity can be introduced by a variety of means, such as chemical modifications of the amino acids.

For example, as one source of added diversity a peptide library of the invention can have its carboxy terminal amidated. Carboxy terminal amidation is necessary to the activity of many naturally occurring bioactive peptides. This modification occurs in vivo through cleavage of the N—C bond of a carboxy terminal Gly residue in a two-step reaction catalyzed by the enzymes peptidylglycine alpha-amidation monooxygenase (PAM) and hydroxyglycine aminotransferase (HGAT). See, Eipper et al., *J. Biol. Chem.* 266:7827–7833 (1991); Mizuno et al., *Biochem. Biophys. Res. Comm.* 137(3): 984–991 (1986); Murthy et al., *J. Biol. Chem.* 261(4): 1815–1822 (1986); Katopodis et al., *Biochemistry* 29:6115–6120 (1990); and Young and Tamburini, *J. Am. Chem. Soc.* 111:1933–1934 (1989), each of which are incorporated herein by reference.

Carboxy terminal amidation can be made to a peptide library of the invention which has the variable region exposed at the carboxy terminus. Amidation can be performed by treatment with enzymes, such as PAM and HGAT, in vivo or in vitro, and under conditions conducive to maintaining the structural integrity of the bioactive peptide. In a random peptide library of the present invention, amidation will occur on a library subset, i.e., those peptides having a carboxy terminal Gly. A library of peptides designed for amidation can be constructed by introducing a Gly codon at the end of the variable region domain of the library. After amidation, an enriched library serves as a particularly efficient source of ligands for receptors that preferentially bind amidated peptides.

Many of the C-terminus amidated bioactive peptides are processed from larger pro-hormones, where the amidated peptide is flanked at its C-terminus by the sequence -Gly-Lys-Arg-X . . . (where X is any amino acid). In the present invention, oligonucleotides encoding the sequence -Gly-Lys-Arg-X-Stop are placed at the 3' end of the variable oligonucleotide region. When expressed, the Gly-Lys-Arg-X is removed by in vivo or in vitro enzymatic treatment and the peptide library is carboxy terminal amidated as described above.

Another means to add to the library diversity through carboxy terminal amidation involves the use of proteins that typically have an exposed C terminus, i.e., a protein that crosses a membrane with its carboxy terminus exposed on the extracellular side of the membrane. In this embodiment the variable oligonucleotide region, having a stop codon in the last position, is inserted in the 3' end of a sequence which encodes C terminus exposed protein, or at least a portion of the protein that is responsible for the C-terminus out orientation. The transferrin receptor protein is an example of one such protein. This receptor has been cloned and sequenced, as reported in McClelland et al., *Cell* 39:267–274 (1984), incorporated herein by reference. An internal transmembrane segment of the transferrin receptor serves to orient the protein with its carboxy terminus out. When the cDNA is expressed, typically in eucaryotic cells, the random peptides are located extracellularly, having their amino terminus fused to the transferrin receptor and with a free carboxy terminus.

For carboxy terminal peptide libraries, a COS cell expression cloning system can also be used and may be preferred in some circumstances. COS cells are transfected with a variable nucleotide library contained in an expression plasmid that replicates and produces mRNA extrachromosomally when transfected into COS cells. Transfected cells bearing the random peptides are selected on immobilized ligand or cells which bear a binding protein, and the plasmid is isolated (rescued) from the selected cells. The plasmid is then amplified and used to transfect COS cells for a second round of screening. Because the random oligonucleotides are inserted directly into the expression plasmid, much larger libraries (i.e., total number of novel peptides) are constructed. Of course, for each round of panning the plasmid needs to be rescued from the COS cells, transfected into bacteria for amplification, re-isolated and transfected back into COS cells.

Other expression systems for carboxy terminal amidation of peptides of the invention can also be used. For example, the variable oligonucleotide sequences are inserted into the 3' end of, e.g., the transferrin receptor cDNA contained in a baculovirus transfer vector. Viral DNA and transfer vector are co-transfected into insect cells (e.g., Sf9 cells) which are used to propagate the virus in culture. When transferrin receptor is expressed, cells harboring recombinant virus, i.e., those producing the transferrin receptor/variable peptide fusion protein, are selected using an anti-transferrin receptor monoclonal antibody linked to a particle such as magnetic microspheres or other substance to facilitate separation. The selected cells are further propagated, allowed to lyse and release the library of recombinant extracellular budded virus into the media.

The library of recombinant virus is amplified (e.g., in Sf9 cells), and aliquots of the library stored. Sf9 cells are then infected with the library of recombinant virus and panned on immobilized target receptor, where the panning is timed to occur with transferrin receptor expression. The selected cells are allowed to grow and lyse, and the supernatant used to infect new Sf9 cells, resulting in amplification of virus that encodes peptides binding to the target receptor. After several rounds of panning and amplification, single viruses are cloned by a Sf9 cell plaque assay as described in Summers and Smith, *A Manual of Methods for Baculovirus Vectors and Insect Cell Culture Procedures*, Texas Agricultural Experiment Station Bulletin No. 1555 (1988), incorporated herein by reference. DNA in the variable oligonucleotide insert region is then sequenced to determine the peptides which bind to the target receptor.

An advantage of the baculovirus system for peptide library screening is that expression of the transferrin receptor/random peptide fusion protein is very high (>1 millions receptors per cell). A high expression level increases the likelihood of successful panning based on stoichiometry and/or contributes to polyvalent interactions with an immobilized target receptor. Another advantage of the baculovirus system is that, similar to the peptide on phage method, infectivity is exploited to amplify virus which is selected by the panning procedure. During the series of pannings, the DNA does not need to be isolated and used for subsequent transfections of cells.

Other expression systems can be employed in the present invention. As eucaryotic signal sequences are operable in yeast and bacteria, proteins with a carboxy terminus out orientation, such as the transferrin receptor, can be appropriately expressed and oriented in yeast or bacteria. The use of yeast or bacteria allows large libraries and avoids potential problems associated with amplification.

Other modifications found in naturally occurring peptides and proteins can be introduced into the libraries to provide additional diversity and to contribute to a desired biological activity. For example, the variable region library can be provided with codons which code for amino acid residues involved in phosphorylation, glycosylation, sulfation, isoprenylation (or the addition of other lipids), etc. Modifications not catalyzed by naturally occurring enzymes can be introduced by chemical means (under relatively mild conditions) or through the action of, e.g., catalytic antibodies and the like. In most cases, an efficient strategy for library construction involves specifying the enzyme (or chemical) substrate recognition site within or adjacent to the variable nucleotide region of the library so that most members of the library are modified. The substrate recognition site added could be simply a single residue (e.g., serine for phosphorylation) or a complex consensus sequence, as desired.

Conformational constraints, or scaffolding, can also be introduced into the structure of the peptide libraries. A number of motifs from known protein and peptide structures can be adapted for this purpose. The method involves introducing nucleotide sequences that code for conserved structural residues into or adjacent to the variable nucleotide region so as to contribute to the desired peptide structure. Positions nonessential to the structure are allowed to vary.

A degenerate peptide library as described herein can incorporate the conserved frameworks to produce and-/or identify members of families of bioactive peptides or their binding receptor elements. Several families of bioactive peptides are related by a secondary structure that results in a conserved "framework," which in some cases is a pair of cysteines that flank a string of variable residues. This results in the display of the variable residues in a loop closed by a disulfide bond, as discussed above.

In some cases a more complex framework is shared among members of a peptide family which contributes to the bioactivity of the peptides. An example of this class is the conotoxins, peptide toxins of 10 to 30 amino acids produced by venomous molluscs known as predatory cone snails. The conotoxin peptides generally possess a high density of disulfide cross-linking. Of those that are highly cross-linked, most belong to two groups, mu and omega, that have conserved primary frameworks as follows:

| mu | CC.....C.....C.....CC; and |
| omega | C.....C.....CC.....C.....C |

The number of residues flanked by each pair of C's varies from 2 to 6 in the peptides reported to date. The side chains of the residues which flank the Cys residues are apparently not conserved in peptides with different specificity, as in peptides from different species with similar or identical specificities. Thus, the conotoxins have exploited a conserved, densely cross-linked motif as a framework for hypervariable regions to produce a huge array of peptides with many different pharmacological effects.

The mu and omega classes (with 6 C's) have 15 possible combinations of disulfide bonds. Usually only one of these conformations is the active ("correct") form. The correct folding of the peptides may be directed by a conserved 40 residue peptide that is cleaved from the N-terminus of the conopeptide to produce the small, mature bioactive peptides that appear in the venom.

With 2 to 6 variable residues between each pair of C's, there are 125 ($5^3$) possible framework arrangements for the mu class (2,2,2, to 6,6,6), and 625 ($5^4$) possible for the omega (2,2,2,2 to 6,6,6,6). Randomizing the identity of the residues within each framework produces $10^{10}$ to $> 10^{30}$ peptides. "Cono-like" peptide libraries are constructed having a conserved disulfide framework, varied numbers of residues in each hypervariable region, and varied identity of those residues. Thus, a sequence for the structural framework for use in the present invention comprises Cys-Cys-Y-Cys-Y-Cys-Cys, or Cys-Y-Cys-Y-Cys-Cys-Y-Cys-Y-Cys, wherein Y is (NNK)$_x$ or (NNS)$_x$, and where N is A, C, G or T, K is G or T, S is G or C, and x is from 2 to 6.

Other changes can be introduced to provide residues that contribute to the peptide structure, around which the variable amino acids are encoded by the library members. For example, these residues can provide for $\alpha$-helices, a helix-turn-helix structure, four helix bundles, etc., as described.

Another exemplary scaffold structure takes advantage of metal ion binding to conformationally constrain peptide structures. Properly spaced invariant metal ligands (cysteines and histidines) for certain divalent cations (e.g., zinc, cobalt, nickel, cadmium, etc.) can be specifically incorporated into the peptide libraries. Depending on the particular motif specified these can result (in the case of zinc coordination, for example) in zinc loops, zinc fingers, zinc twists, or zinc clusters, as generally described in Berg (*J. Biol. Chem.* 265:6513–6516 (1990)), Green et al. (*Proc. Natl. Acad. Sci. USA*, 86:4047–4051 (1989)), Parraga et al. (*Science* 241:1489–1492 (1988)), Regan et al. (*Biochem.*, 29:10878–10883 (1990)), and Vallee et al. (*Proc. Natl. Acad. Sci. USA*, 88:999–1003 (1991)), each incorporated herein by reference. Other DNA binding peptides, such as those which correspond to the transcriptional transactivators referred to as leucine zippers, can also be used as a framework, where leucine residues are repeated every seven residues in the motifs, and the region is adjacent to an alpha helical region rich in lysines and arginines and characterized by a conserved helical face and a variable helical face.

Other specialized forms of structural constraints can also be used in the present invention. For example, certain serine proteases are inhibited by small proteins of conserved structure (e.g., pancreatic trypsin inhibitor). This conserved framework can incorporate degenerate regions as described herein to generate libraries for screening for novel protease inhibitors.

In another aspect related to frameworks for a peptide library, information from the structure of known ligands can be used to find new peptide ligands having features modified from those of the known ligand. In this embodiment, fragments of a gene encoding a known ligand, prepared by, e.g., limited DNAse digestion into pieces of 20 to 100 base pairs, are subcloned into a variable nucleotide region system as described herein either singly or in random combinations of several fragments. The fragment library is then screened in accordance with the procedures herein for binding to the receptor to identify small peptides capable of binding to the receptor and having characteristics which differ as desired from the parental peptide ligand. This is useful for screening for any receptor-ligand interaction where one or both members are encoded by a gene, e.g., growth factors, hormones, cytokines and the like, such as insulin, interleukins, insulin-like growth factor, etc.

The peptide-phage libraries of the present invention can also be used to determine the site specificity of enzymes that modify proteins, e.g., the cleavage specificity of a protease. For example, factor $X_a$ cleaves after the sequence Ile-Glu-Gly-Arg. A library of variable region codons as described herein is constructed having the structure: signal sequence—variable region—Tyr- Gly-Gly-Phe-Leu—pIII. Phage from the library are then exposed to factor $X_a$ and then panned on an antibody (e.g., 3E7), which is specific for N-terminally exposed Tyr-Gly-Gly-Phe-Leu. A pre-cleavage panning step with 3E7 can be employed to eliminate clones cleaved by *E. coli* proteases. Only members of the library with random sequences compatible with cleavage with factor $x_a$ are isolated after panning, which sequences mimic the Ile-Glu-Gly-Arg site.

Another approach to protease substrate identification involves placing the variable region between the carrier protein and a reporter sequence that is used to immobilize the complex (e.g., Tyr-Gly-Gly-Phe-Leu). Libraries are immobilized using a receptor that binds the reporter sequence (e.g., 3E7 antibody). Phage clones having sequences compatible with cleavage are released by treatment with the desired protease.

Some peptides, because of their size and/or sequence, may cause severe defects in the infectivity of their carrier phage. This causes a loss of phage from the population during reinfection and amplification following each cycle of panning. To minimize problems associated with defective infectivity, DNA prepared from the eluted phage is transformed into appropriate host cells, such as, e.g., *E. coli*, preferably by electroporation, as described in, for example, Dower et al., *Nucl. Acids Res.* 16:6127–6145 (1988), incorporated herein by reference, or by well known chemical means. The cells are cultivated for a period of time sufficient for marker expression, and selection is applied as typically done for DNA transformation. The colonies are amplified, and phage harvested for affinity enrichment as described below. Phage identified in the affinity enrichment can be re-amplified in additional rounds of propagation by infection into appropriate hosts.

The successful transformants are typically selected by growth in a selective medium or under selective conditions, e.g., an appropriate antibiotic, which, in the case of the fd-tet vector, is preferably tetracycline. This may be done on solid or in liquid growth medium. For growth on solid medium, the cells are grown at a high density ($10^8$ to $10^9$ tfs per m$^2$) on a large surface of, for example, L-agar containing the selective antibiotic to form essentially a confluent lawn. The cells and extruded phage are scraped from the surface and phage are prepared for the first round of panning essentially as described by Parmley and Smith, *Gene* 73:30514 318 (1988). For growth in liquid culture, cells may be grown in L-broth and antibiotic through about 10 or more doublings. The phage are harvested by standard procedures (see Sambrooke et al., *Molecular Cloning*, 2nd ed. (1989), supra, for preparation of M13 phage) as described below. Growth in liquid culture may be more convenient because of the size of the libraries, while growth on solid media likely provides less chance of bias during the amplification process.

For affinity enrichment of desired clones, generally about $10^3$ to $10^4$ library equivalents (a library equivalent is one of each recombinant; $10^4$ equivalents of a library of $10^9$ members is $10^9 \times 10^4 = 10^{13}$ phage), but typically at least $10^2$ library equivalents but up to about $10^5$ to $10^6$, are incubated with a receptor (or portion thereof) to which the desired peptides is sought. The receptor is in one of several forms appropriate for affinity enrichment schemes. In one example the receptor is immobilized on a surface or particle, and the library of phage bearing peptide is then panned on the immobilized receptor generally according to the procedure described below.

A second example of receptor presentation is receptor attached to a recognizable ligand (which may be attached via a tether). A specific example of such a ligand is biotin. The receptor, so modified, is incubated with the library of phage and binding occurs with both reactants in solution. The resulting complexes are then bound to streptavidin (or avidin) through the biotin moiety. The streptavidin may be immobilized on a surface such as a plastic plate or on particles, in which case the complexes (phage/peptide/receptor/biotin/streptavidin) are physically retained; or the streptavidin may be labelled, with a fluorophore, for example, to tag the active phage/peptide for detection and/or isolation by sorting procedures, e.g., on a fluorescence-activated cell sorter.

Phage which express peptides without the desired specificity are removed by washing. The degree and stringency of washing required will be determined for each receptor/peptide of interest. A certain degree of control can be exerted over the binding characteristics of the peptides recovered by adjusting the conditions of the binding incubation and the subsequent washing. The temperature, pH, ionic strength, divalent cation concentration, and the volume and duration of the washing will select for peptides within particular ranges of affinity for the receptor. Selection based on slow dissociation rate, which is usually predictive of high affinity, is the most practical route. This may be done either by continued incubation in the presence of a saturating amount of free ligand, or by increasing the volume, number, and length of the washes. In each case, the rebinding of dissociated peptide-phage is prevented, and with increasing time, peptide-phage of higher and higher affinity are recovered. Additional modifications of the binding and washing procedures may be applied to find peptides which bind receptors under special conditions.

Although the phage screening method is highly specific, the procedure generally does not discriminate between peptides of modest affinity (micromolar dissociation constants) and those of high affinity (nanomolar dissociation constants or greater). The ability to select phage bearing peptides with relatively low affinity may be the result of multivalent interaction between a phage/peptide particle and a receptor. For instance, when the receptor is an IgG antibody, each phage bearing peptides may bind to more than one antibody binding site, either by a single phage binding to both sites of single IgG molecule or by forming network of phage-IgG, which multivalent interaction produces a high avidity and tenacious adherence of the phage during washing.

To enrich for the highest affinity peptide ligands, a substantially monovalent interaction between phage and the receptor (typically immobilized on a solid-phase) may thus be appropriate. The screening (selection) with substantially monovalent interaction can be repeated as part of additional rounds of amplification and selection of bacteriophage. Thus, under these circumstances the receptor molecule is substantially monovalent, such as the Fab binding fragment of an antibody molecule.

A strategy employing a combination of conditions favoring multivalent or monovalent interactions can be used to advantage in producing new peptide ligands for receptor molecules. By conducting the first rounds of screening under conditions to promote multivalent interactions, high stringency washing can be used to greatly reduce the background of non-specifically bound phage. This high avidity step may select a large pool or peptides with a wide range of affinities, including those with relatively low affinity. It may select for specific recognition kernels, such as the Tyr-Gly dipeptide described in the examples below. Subsequent screening under conditions favoring increasingly monovalent interactions and isolation of phage based on a slow dissociation rate may then allow the identification of the highest affinity peptides. Monovalent interactions may be achieved by employing low concentrations of receptor (for example, from about 1 to 100 pM).

It should be noted that, as an aspect of the present invention, determining a dissociation rate for a peptide of interest and the selected receptor molecule under substantially monovalent conditions allows one to extrapolate the binding affinity of the peptide for the receptor. This procedure avoids the necessity and inconvenience of separately determining binding affinities for a selected peptide, which could be especially burdensome if a large number of peptides have been selected.

Once a peptide sequence that imparts some affinity and specificity for the receptor molecule is known, the diversity around this "recognition kernel" may be embellished. For instance, variable peptide regions may be placed on one or both ends of the identified sequence. The known sequence may be identified from the literature, as in the case of Arg-Gly-Asp and the integrin family of receptors, for example, as described in Ruoslahti and Pierschbacher, Science 238:491–497 (1987), or may be derived from early rounds of panning in the context of the present invention.

Libraries of peptides on phage produced and screened according to the present invention are particularly useful for mapping antibody epitopes. The ability to sample a large number of potential epitopes as described herein has clear advantages over the methods based on chemical synthesis now in use and described in, among others, Geysen et al., J. Immunol. Meth. 102:259–274 (1987). In addition, these libraries are useful in providing new ligands for important binding molecules, such as hormone receptors, adhesion molecules, enzymes, and the like.

Accordingly, the following examples are offered by way of illustration, not by way of limitation.

EXAMPLE I

Reagents and Strains

BstXI restriction endonuclease, T4 DNA ligase, and T4 kinase were obtained from New England Biolabs. Streptavidin and biotinylated goat anti-mouse IgG were obtained from BRL. Sequenase 2.0 was obtained from U.S. Biochemical. Monoclonal antibody 3E7 used in initial studies was provided by A. Herz and is described in Meo et al., infra., incorporated herein by reference, and was also purchased from Gramsch Laboratories (Schwabhausen, West Germany). [$^{125}$I-tyr$^{28}$]b-endorphin (hereinafter "b-endorphin") (2000 Ci/mmol) was purchased from Amersham Corp. (Arlington Heights, Ill.). Oligonucleotides were synthesized with an Applied BioSystems PCR-Mate and purified on OPC columns (ABI). Peptides were synthesized with an Applied BioSystems 431A (Foster City, Calif.) or Biosearch model 9600 (San Rafael, Calif.) synthesizer and purified to greater than 95% purity by reverse phase HPLC. Peptide content of the pure peptides was determined by amino acid analysis and the composition was verified by FAB-MS. Bacteriophage fd-tet and E. coli K91 were provided by G. Smith, Univ. of Missouri, Columbia, Mo. 65211, and are described in, among others, Zacher et al., Gene 9:127–140 (1980), Smith et al., Science 228:1315–1317 (1985) and Parmley and Smith, Gene 73:305–318 (1988).

Construction of Vector fAFF1

Figures 1A, 1B:
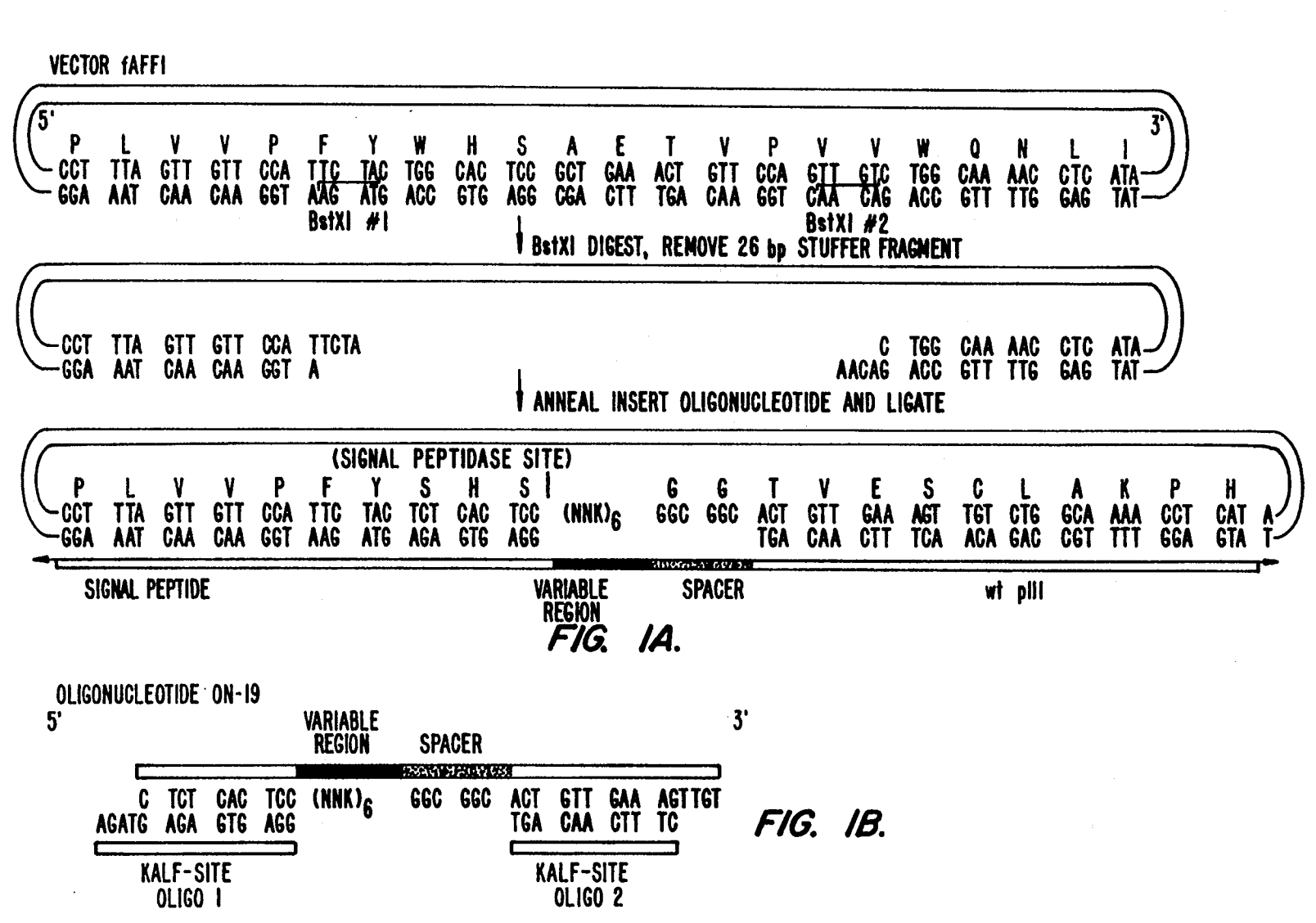

A filamentous bacteriophage vector was constructed from the tetracycline resistance transducing vector fdTet, described in Zacher et al., supra. The vector, designated fAFF1, was designed to provide many choices in the size and location of the peptides expressed fused to the pIII bacteriophage coat protein. pIII is made as a preprotein with an 18 amino acid leader sequence that directs pIII to the inner membrane of the bacterial host cell before it becomes assembled into an intact phage particle (Goldsmith and Konigsberg, Biochem. 16:2686–2694 (1977) and Boeke and Model, Proc. Natl. Acad. Sci. USA 79:5200–5204 (1982) incorporated herein by reference). As explained further below, a peptide library was constructed by cloning an oligonucleotide of the structure shown in FIG. 1B to place the variable hexapeptide region at the N-terminus of the processed protein. These first six residues are followed by two glycines and then the normal sequence of pIII. The library consists of about $3 \times 10^8$ independent recombinants.

A cloning site, consisting of two non-complementary BstXI sites, was engineered into the 5'-region of gene III. As shown in FIG. 1A, two non-complementary BstXI sites flank the region encoding amino acids surrounding the signal peptidase site (the N-terminus of the mature pIII). fAFF1 also has a −1 frameshift mutation in pIII that results in non-infective phage. By removing the BstXI fragment and inserting an oligonucleotide of the appropriate structure, (a) portions of the removed sequence can be precisely reconstructed (the correct signal peptide site, for example,) (b) one or more additional amino acids may be expressed at several locations, and (c) the correct translation frame is restored to produce active, infective pIII.

Construction of the cloning site at the 5'-region of gene III was accomplished by first removing a BstXI restriction site already present in the TN10 region of fdTet, RF DNA was digested with BstXI restriction endonuclease, and T4 DNA polymerase was added to remove the protruding 3' termini. Blunt-ended molecules were then ligated and transformed into MC1061 cells. RF DNA isolated from several tetracycline resistant transformants was digested again with BstXI; a clone that was not cleaved was selected for construction of the double BstXI site. Site-directed mutagenesis (Kunkel et al., Meth. Enzymol. 154:367–382 (1987), incorporated by reference herein) was carried out with the oligonucleotide 5'-TAT GAG GTT TTG CCA GAC AAC TGG AAC AGT TTC AGC GGA GTG CCA GTA GAA TGG AAC AAC TAA AGG. Insertion of the correct mutagenic sequence was confirmed by dideoxy sequencing of RF DNA isolated from several tetracycline-resistant transformants.

Construction of a Diverse Oligonucleotide Library

Oligonucleotides which were cloned have the general structure shown in Fig. 1B. The 5' and 3' ends have a fixed sequence, chosen to reconstruct the amino acid sequence in the vicinity of the signal peptidase site. The central portion contained the variable regions which comprise the oligonucleotide library members, and may also code for spacer residues on either or both sides of the variable sequence.

A collection of oligonucleotides encoding all possible hexapeptides was synthesized with the sequence 5'-C TCT CAC TCC (NNK) 6 GGC GGC ACT GTT GAA AGT TGT-3'. N was A, C, G, and T (nominally equimolar), and K was G and T (nominally equimolar). This sequence, designated ON-49, was ligated into the BstXI sites of fAFF1 after annealing to two "half-site" oligonucleotides, ON-28 (5'-GGA GTG AGA GTA GA-3') and ON-29 (5'-CTT TCA ACA GT-3'), which are complementary to the 5'- and 3'- portions of ON-49, respectively. Half-site oligonucleotides anneal to the 5'- and 3'- ends of oligonucleotide 0N-49 to form appropriate BstXI cohesive ends. This left the appropriate BstXI site exposed without the need to digest with BstXI, thus avoiding the cutting of any BstXI sites that might have appeared in the variable region. The vector fAFF1 (100 μg) was digested to completion with BstXI, heat inactivated at 65° C., and ethanol precipitated twice in the presence of 2M ammonium acetate. Oligonucleotides were phosphorylated with T4 kinase, and annealed in 20 mM Tris-HCl, pH 7.5, 2 mM MgCl$_2$, 50 mM NaCl, by mixing 1.5 μg ON-28, 1.2 μg ON-29, and 0.5 μg ON-49 with 20 μg BstXI-digested fAFF1 RF DNA, heating to 65° C. for 5 minutes and allowing the mixture to cool slowly to room temperature. This represented an approximate molar ratio of 1:5:100:100 (fAFF1 vector: ON-49: ON-28: ON-29). The annealed structure is then ligated to BstXI-cut fAFF1 RF DNA to produce a double-stranded circular molecule with a small, single stranded gap. These molecules may be transformed into host cells. The annealed DNA was ligated in 20 mM Tris-HCl, pH 7.5, 5 mM MgCl$_2$, 2 mM DTT, 1 mMATP, by the addition of 20 units of T4 DNA ligase and incubated overnight at 15° C.

Alternatively, before transformation, the gap may be filled-in under conditions disfavoring secondary structure in the variable region. In some experiments the gapped circular structure created by this ligation was filled in with T4 DNA polymerase in the presence of ligase and dNTPs (400 μM each) to produce a covalently closed, double-stranded molecule (Kunkel et al., supra). The ligated DNA was ethanol precipitated in the presence of 0.3M sodium acetate, resuspended in water, and transformed by electroporation into MC1061. Five electro-transformations, each containing 80 μl of cells and 4 μg of DNA (50 g/ml), were performed by pulsing at 12.5 kV/cm for 5 msec as described in Dower et al., *Nucleic Acids Res.* 16:6127–6145 (1988), incorporated by reference herein. After one hour of non-selective outgrowth at 37° C. in 2 ml of SOC medium (2% Bacto tryptone, 0.5% Bacto yeast extract, 10 mM NaCl, 2.5 mM KCl, 10 mM MgCl$_2$, 10 mM MgSO$_4$, 20 mM glucose; see Hanahan, *J. Mol. Biol.* 166:557–580 (1983)), the transformations were pooled, an aliquot was removed, and several dilutions were plated on LB agar plates containing tetracycline (20 μg/ml) to assess the transformation efficiency. The remainder was used to inoculate one liter of L-broth containing tetracycline (20 μg/ml) and was grown through approximately 10 doublings at 37° C. to amplify the library.

Isolation of Phage

Phage from liquid cultures were obtained by clearing the supernatant twice by centrifugation (8000 RPM for 10 min in JA10 rotor, at 4°), and precipitating phage particles with polyethylene glycol (final concentration 3.3% polyethylene glycol-8000, 0.4M NaCl), and centrifuged as described above. Phage pellets were resuspended in TBS (50 mM Tris-HCl, pH 7.5, 150 mM NaCl) and stored at 4° C. In some cases, phage were isolated from plate stocks by scraping from the agar surface, resuspending in L-broth, and purifying as described above.

Affinity Purification

Approximately $10^3$ to $10^4$ library equivalents of phage were reacted overnight with 1 μg of purified antibody in 1 ml TBS at 4° C. (Under these conditions, phage and antibody are about equimolar; therefore, antibody is in great excess over the phage ligand peptides.) Phage expressing peptides with affinity for mAb3E7 were isolated by a modification of the procedure of Parmley and Smith, supra. A 60×15 mm polystyrene petri plate was coated with 1 ml of streptavidin solution (1 mg/ml streptavidin in 0.1M NaHC$_3$, pH 8.6, 0.02% NAN$_3$) and incubated overnight at 4° C. The streptavidin solution was removed the following day. The plate was filled with 10 ml blocking solution (30 mg/ml BSA, 3 μg/ml streptavidin in 0.1M NaHCO$_3$, pH 9.2, 0.02% NAN$_3$) and incubated for two hours at room temperature. Biotinylated goat anti-mouse IgG (2 μg) was added to the antibody-reacted phage library and incubated for two hours at 4° C. Immediately before panning, the blocking solution was removed from the streptavidin-coated plate, and the plate was washed 3 times with TBS/0.05% Tween 20. The antibody-reacted phage library was then added to the plate and incubated for 30 min. at room temperature. The phage solution was removed and the plate was washed ten times with 10 ml TBS/0.05% Tween 20 over a period of 60 min. at room temperature. Adherent phage were removed by adding 800 μl of elution buffer (1 mg/ml BSA in 0.1N HCl adjusted to pH 2.2 with glycine) to the petri plate and incubating for 10 min. to dissociate the immune complexes. The eluate was removed, neutralized by addition of 45 μl of 2M Tris base, and used to infect log phase *E. coli* K91 cells.

The infected cells were then plated on LB agar plates containing tetracycline (20 μg/ml), and grown overnight at 37° C. Phage were isolated from these plates as described above and the affinity purification process was repeated for two more rounds. After each round of panning and amplification, DNA of phage from several thousand colonies was pooled and sequenced to estimate the diversity in the cloning site. In the first two positions of each codon, bands of about the same intensity appeared in each lane, indicating the expected distribution of bases in these positions. In the third position of each codon the G band was somewhat more intense than the T band.

After the final round of panning and amplification, a portion of the eluate was used to infect cells that were plated at low density on LB tetracycline plates. To analyze the diversity of peptide sequences in the library in a more direct way, we picked 52 individual colonies producing infectious phage, and sequenced the DNA of their variable regions. Individual colonies were picked and transferred to culture tubes containing 2 ml LB tetracycline and grown to saturation. Phage DNA was isolated and then sequenced by a method designed for the Beckman Biomek Workstation employing 96-well microtiter plates (Mardis and Roe, *Biotechniques* 7:840–850 (1989), incorporated by reference herein). Single stranded DNA was sequenced using Sequenase 2.0 and an oligonucleotide sequencing primer (5'-CGA TCT AAA GTT TTG TCG TCT-3') which is complementary to the sequence located 40 nucleotides to the 3' side of the second BstXI site in fAFF1.

The distribution of bases at each position within each codon is given in Table 1. The first two positions of each codon have close to the expected equimolar distribution of the four bases. The third position is significantly biased, containing about 50% more G than T in this sample. This bias is most likely introduced during the chemical synthesis of the oligonucleotide mixture, but may also reflect biological biases imposed on the expressed peptides.

TABLE 1

Nucleotide Distribution in the Diversity Region of Infectious Phage Randomly chosen from the Library.

Frequency of each base by position in codon (%)

|   | N  | N  | K   |
|---|----|----|-----|
| G | 31 | 27 | 59  |
| A | 22 | 22 | <1  |
| T | 25 | 26 | 39  |
| C | 22 | 24 | 1   |

Figure 2:
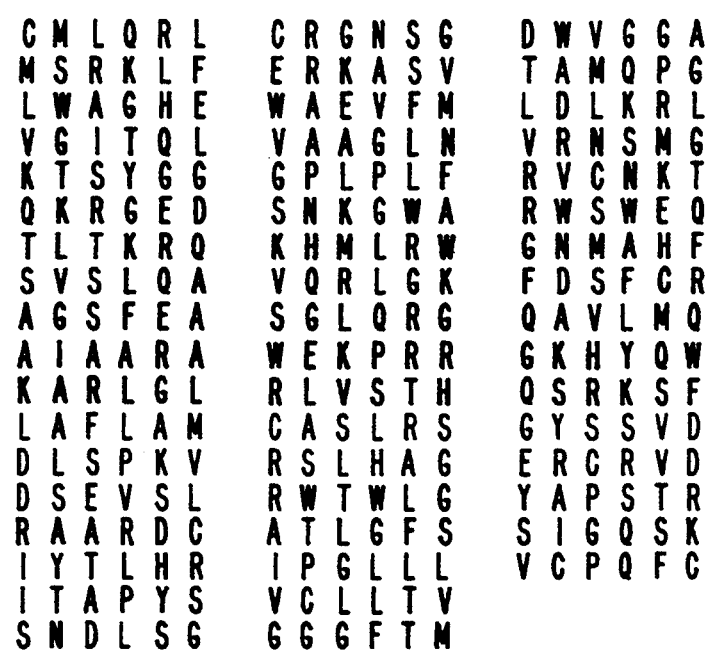

In FIG. 2, the amino acid sequences are listed for the peptides encoded by the oligonucleotide inserts of a sample of randomly chosen, infectious phage. The amino acid content of the expressed peptides from the 52 randomly chosen infectious phage appears in Table 2.

TABLE 2

Amino Acid Content in the Variable Peptide of 52 Randomly-Chosen Infectious Phage

| Amino Acid | Nominal Frequency | Nominal Occurrence | Observed Occurrence | Obs/Nom |
|---|---|---|---|---|
| A | 0.065 | 19 | 27 | 1.42 |
| C | 0.032 | 9  | 8  | 0.89 |
| D | 0.032 | 9  | 10 | 1.11 |
| E | 0.032 | 9  | 9  | 1.00 |
| F | 0.032 | 9  | 12 | 1.33 |
| G | 0.065 | 19 | 33 | 1.74 |
| H | 0.032 | 9  | 7  | 0.78 |
| I | 0.032 | 9  | 6  | 0.67 |
| K | 0.032 | 9  | 16 | 1.78 |
| L | 0.097 | 28 | 35 | 1.25 |
| M | 0.032 | 9  | 10 | 1.11 |
| N | 0.032 | 9  | 7  | 0.78 |
| P | 0.065 | 19 | 9  | 0.47 |
| Q | 0.032 | 9  | 15 | 1.67 |
| R | 0.097 | 28 | 29 | 1.04 |
| S | 0.097 | 28 | 30 | 1.07 |
| T | 0.065 | 19 | 14 | 0.74 |
| V | 0.065 | 19 | 18 | 0.95 |
| W | 0.032 | 9  | 11 | 1.22 |
| Y | 0.032 | 9  | 6  | 0.67 |

As shown in Table 2, the ratio of the observed occurrence of each amino acid to that expected on the basis of codon frequency ranges from about 0.5 to 2, consistent with a random distribution of sequences.

Constructing a library of peptides displayed on the N-terminus of processed pIII necessarily alters amino acids in the vicinity of the signal peptidase cleavage site. Certain changes in the corresponding region of the major coat protein, pVIII, have been shown to reduce processing efficiency, slowing or preventing the incorporation of pVIII to virions. If pIII were similarly affected, the diversity of peptides contained in the library would be reduced. The finding that most amino acids appear at each position of the variable peptides of randomly chosen phage indicates that processing defects do not impose severe constraints on the diversity of the library.

Isolation and sequencing of phage having high avidity for anti-b-endorphin antibody.

Monoclonal antibody 3E7 binds to B-endorphin and, like the δ-opioid receptor, recognizes the N-terminal portion of the protein (Tyr-Gly-Gly-Phe), which is present on most natural opioid peptides. The antibody also binds tightly to leu- and met-enkephalin (YGGFL, YGGFM), and a variety of related opioid peptides (Meo et al., *Proco Natl. Acad. Sci. USA* 80:4084–4088 (1983), Herz et al., *Life Sciences* 31:1721–1724 (1982), and Gramsch et al., *J. Neurochem.* 40:1220–1226 (1983). The N-terminal hexapeptide library was screened against 3E7 by carrying out three rounds of panning, elution, and amplification. The recoveries of phage from this process are shown in Table 3. In each round the proportion of phage adsorbed to the antibody increased by about 100-fold, and in the last round, over 30% of the input phage were recovered. These results indicated that phage were preferentially enriched in each panning step.

TABLE 3

Recovery of Phage from Panning on mAb3E7

| Rounds of Panning | Input of Phage | Eluted Phage | Recovery Input/Eluted |
|---|---|---|---|
| 1 | $4.0 \times 10^{11}$ | $1.9 \times 10^{7}$ | $4.8 \times 10^{-5}$ |
| 2 | $2.0 \times 10^{11}$ | $5.0 \times 10^{8}$ | $2.5 \times 10^{-3}$ |
| 3 | $1.8 \times 10^{10}$ | $5.6 \times 10^{9}$ | $3.1 \times 10^{-1}$ |

After each round of panning, DNA representing several thousand eluted phage was pooled and sequenced. The area of the sequencing gel corresponding to the insertion site in gene III is shown in FIG. 3. The codon TCC specifying the serine that precedes the variable region is indicated by an arrow. After the first round of panning, the codon following this serine codon was clearly enriched in TAT (the single codon for tyrosine). After the second round, virtually all first codons in the pooled DNA appeared to be TAT. The second codons are strongly GGK (the two codons for glycine). After three rounds of panning, it appeared that phage containing relatively few kinds of amino acids in the first four positions had been selected, whereas the fifth and sixth positions appeared to be as diverse as those in the starting phage population.

The DNA samples from 52 individual phage recovered from the third panning were sequenced. The deduced amino acid sequences of the N-terminal hexapeptides are shown in FIG. 4 and the amino acid distributions of these peptides are summarized in Table 4. Each of the 52 panned phages analyzed had an N-terminal tyrosine, and nearly all (94%) had a glycine in the second position. The third position in our sample is occupied by many amino acids, some of which are present more often than would be expected by chance. The fourth position is occupied primarily by the large aromatic residues Trp and Phe (together 50%), and the bulky hydrophobic residues Leu and Ile (an additional 45%). The fifth and sixth positions contain essentially random distributions of amino acids, with only alanine appearing at slightly greater than chance in position five.

TABLE 4

Distribution of Amino Acids in the Diversity Peptide of 52 Phage Selected by Panning With Anti-endorphin Antibody

| Position | Amino Acid | Nominal | Observed Frequency | Residue Enrichment[a] Ratio Frequency |
|---|---|---|---|---|
| 1 | Y | .031 | 1.00 | 33 |
| 2 | G | .062 | 0.94 | 16 |
|   | A,S |      |      | <1 |
| 3 | G | .062 | 0.31 | 5 |
|   | W | .031 | 0.10 | 3 |
|   | S | .093 | 0.21 | 2 |
|   | A | .062 | 0.12 | 2 |
|   | N | .031 | 0.06 | 2 |
|   | D,E,F,K,L,M,P,T,V |  |  | <1 |
| 4 | W | .031 | 0.31 | 10 |
|   | F | .031 | 0.19 | 6 |
|   | L | .093 | 0.35 | 4 |
|   | I | .031 | 0.10 | 3 |
|   | A,G,M |  |  | <1 |

[a] Observed frequency divided by nominal frequency.

EXAMPLE II

Binding Affinities of Peptides for Receptor Monoclonal Antibody 3E7

The affinities of peptides for the 3E7 antibody have been previously determined for those peptides related to naturally-occurring opioid peptides. Meo et al., supra. As none of the peptides identified by the procedure described herein had been previously described, six of these peptides were chemically synthesized and their binding affinities estimated.

The peptides were synthesized according to well known protocols, as described in, for example, Merrifield, Science 232:341–347 (1986), incorporated by reference herein. A solution radioimmunoassay was used to estimate the binding affinities of peptides for mAb 3E7. Solution radioimmunoassay using [$^{125}$I]b-endorphin (20,000 cpm) and purified 3E7 antibody (0.25 μg/ml) was conducted as described by Meo et al., supra, with the exception that the final volume was 150 μl. Antibody-bound and free [$^{125}$I]b-endorphin were separated by addition of activated charcoal followed by centrifugation, as described in Ghazarassian et al., Life Sciences 27:75–86 (1980). Antibody-bound [$^{125}$I]b-endorphin in the supernatant was measured in a gamma counter. For each peptide, inhibition of [$^{125}$I]b-endorphin was determined at six different concentrations at ⅓ log unit intervals and the 50% inhibitory concentration (IC50) was determined by fitting the data to a two-parameter logistic equation using the ALLFIT program, as described in DeLean et al., Am. J. Phsiol. 235:E97–E102 (1978).

The previously reported high degree of specificity of the 3E7 antibody for the intact N-terminal epitope Tyr-Gly-Gly-Phe which is common to naturally occurring opioid peptide, Meo et al., supra, was verified. Removal of Tyr or deletion of any of the amino acids of the sequence Tyr-Gly-Gly-Phe-Leu had deleterious effect on binding affinity (Table 5).

Shown in Table 5 are the IC50 for the six peptides which were identified by the phage panning method and chemically synthesized. Under the conditions of the radioimmunoassay (30 pM [$^{125}$I]b-endorphin; 20% tracer bound; 18 hr. incubation), the IC50 should be very close to the dissociation constant (Kd) for the peptide. The peptides are all relatively low affinity compared to YGGFL, with IC50's ranging from 0.35 to 8.3 μM.

TABLE 5

Relative affinities of peptides for 3E7 antibody determined by solution radioimmunoassay.[a]

| Peptide | N | IC50 (μM) | Affinity Relative to YGGFL |
|---|---|---|---|
| YGGFL | (6) | 0.0071 (0.0054, 0.0093) | 1 |
| YGGF | (3) | 0.19 (0.093, 0.38) | 0.037 |
| YGGL | (3) | 3.8 (2.1, 6.6) | 0.0018 |
| YGFL | (3) | 28 (17, 47) | 0.00025 |
| YGG | (2) | >1000 | <0.0000071 |
| GGFL | (2) | >1000 | <0.0000071 |
| GGF | (2) | >1000 | <0.0000071 |
| GFL | (2) | >1000 | <0.0000071 |
| YGFWGM | (3) | 0.35 (0.19, 0.63) | 0.020 |
| YGPFWS | (3) | 1.9 (1.3, 2.8) | 0.0037 |
| YGGFPD | (3) | 2.3 (1.4, 3.7) | 0.0031 |
| YGGWAG | (3) | 7.8 (6.0, 10) | 0.00091 |
| YGNWTY | (3) | 7.8 (4.0, 15) | 0.00091 |
| YAGFAQ | (3) | 8.3 (3.8, 18) | 0.00086 |

[a] = Data are geometric means and 95% confidence intervals (calculated from S.E.M. of log IC50) from the number (N) of independent determinations indicated.

The data indicate that although the phage panning method is highly specific in that no unrelated peptides were selected, the procedure apparently does not discriminate between those of moderate (μM Kd) and high (nM Kd) affinity. The six peptides chosen from among the 52 clones that were sequenced were only a small subset of those which were selected by three rounds of panning. Based on their structural diversity, the phage library should contain thousands of different peptides with dissociation constants that are μM or lower.

The panning procedure we have utilized employs extensive washing to remove non-specifically bound phage. Binding experiments with mAb 3E7 and [$^3$H]YGGFL indicate a rapid dissociation rate, approximately t½=45 seconds at room temperature. Therefore, the ability to select phage bearing peptides with relatively low affinities may be the result of multivalent interaction between phage and antibody, as each phage typically has up to 4 or 5 copies of the pIII protein and each protein may carry a foreign peptide from the phage library.

EXAMPLE III

Selective Enrichment and Characterization of High Affinity Lands from Collections of Random Peptides on Phage Phage bearing peptides YGGFL and YAGFAQ served as models to determine the effect of IgG and Fab concentration on the binding and recovery of phage bearing high (nM Kd) and low (μM Kd) affinity peptides.

To determine the effect of polyvalency, a phage sandwich ELISA was developed which used polyclonal anti-phage antibodies to detect bound phage. Purified monoclonal antibody 3E7 was used as intact IgG and as Fab fragments (produced using a commercially available kit (Pierce), and biotinylated Fab fragments (Gramsch Laboratories). No IgG was detected in Fab preparations when they were run on SDS-PAGE gels and stained with Coomassie blue. Fab was iodinated by reacting 5 μg of Fab in 20 μl of 0.1M borate buffer (pH 8.5) with 250 μCi of [$^{125}$I]Bolton-Hunter reagent (Amersham) for 3 hours and then purified by gel filtration on Sephadex G25. After purification, the specific activity of the [$^{125}$I]FAB was approximately 15 μCi/μg.

Antisera were raised against phage particles lacking pIII fAFF1, which, as described above, contains a frameshift in the 5end of gene III and is produced as non-infective polyphage. Cells from a two liter culture of E. coli K91 were removed by centrifugation and media was mixed with 400 ml of 20% PEG in 0.5M NaCl. After incubation for 1 hr at 4 C. precipitated phage were isolated by centrifugation at 8500 rpm. The pellet was resuspended in TBS (50 mM Tris-HCl, 150 mM NaCl, pH 7.4) and then ultracentrifuged in a SW50 rotor at a 42,000 rpm for 3 hrs. The resulting pellet was resuspended in water and the concentration of phage was estimated according to the method of Day, *J. Mol. Biol.* 39:265 (1969).

Three rabbits were injected intramuscularly with 0.5 mg of phage in Freunds complete adjuvant and then boosted with 0.25 mg of phage in incomplete adjuvant at 3 week intervals. The titer of the sera was measured with an ELISA using phage immobilized in Immulon 2 microtiter wells as described above. All rabbits produced high titer sera after the second boost. Sera collected after the third boost from one of the rabbits was used for the assays.

Antibodies reacting with phage were affinity purified as follows. Phage expressing native pIII (Fd-tet) from a two liter culture were isolated (described above) and added to 20 ml of sera that was diluted 4-fold with PBS (10 mM sodium phosphate, 150 mM NaCl, pH 7.4). After incubation for 2 hr at room temperature, phage/antibody complex was isolated by centrifugation for 1 hr at 120,000×g. The pellet was washed with 10 ml of PBS and centrifuged again. The final pellet was resuspended in 10 ml of 100 mM sodium acetate buffer pH 2.5 and incubated for 10 min. at room temp. The sample was subjected to same centrifugation and the resulting supernatant was neutralized with NaOH. IgG was then isolated using Protein-A agarose (Pierce) according to the manufacturer's instructions. The IgG was conjugated to alkaline phosphatase using a commercially available kit (Pierce).

The phage sandwich ELISAs were performed as follows. Microtiter wells were incubated with 100 μg/ml of streptavidin for 1 hr at 37° C., then blocked with 200 μl of PBS/0.1% bovine serum albumin (BSA) for 1 hr. Biotinylated IgG (0.5 μg/ml) or biotinylated Fab (5 g/ml) (100 ml in PBS/0.1% BSA) was added to the wells and incubated for an additional 1 hr at room temperature. Preliminary studies in which immobilized IgG or Fab was detected with goat anti-mouse IgG conjugated to alkaline phosphatase indicated that these conditions maximally saturated the well with IgG or Fab. The difference in concentration for biotinylated IgG and Fab required for saturation of the streptavidin probably reflected differences in the fraction of the protein that was biotinylated.

After washing the wells with PBS, 50 μl of PBS/0.1% BSA/0.05% Tween 20 or the same buffer containing 200 μM YGGFL free peptide was added to the well and incubated for 20 min at room temperature. Phage ($10^{10}$ infectious particles in 50 μl PBS/0.1% BSA/0.05 Tween 20) bearing the peptides YGGFL or YAGFAQ were added and incubated for 18 hr at 4 C. After washing with TBS/0.05% Tween 20, alkaline phosphatase anti-phage antibody (100 μl of 1:100 dilution) was added and incubated for 1 hr at room temperature. After washing with TBS/0.05% Tween 20, 100 μl of alkaline phosphatase substrate (SIGMA) in diethanolamine buffer (pH 9.5) was added and the absorbance at 405 nm was measured 10 min. later.

Figure 5A:
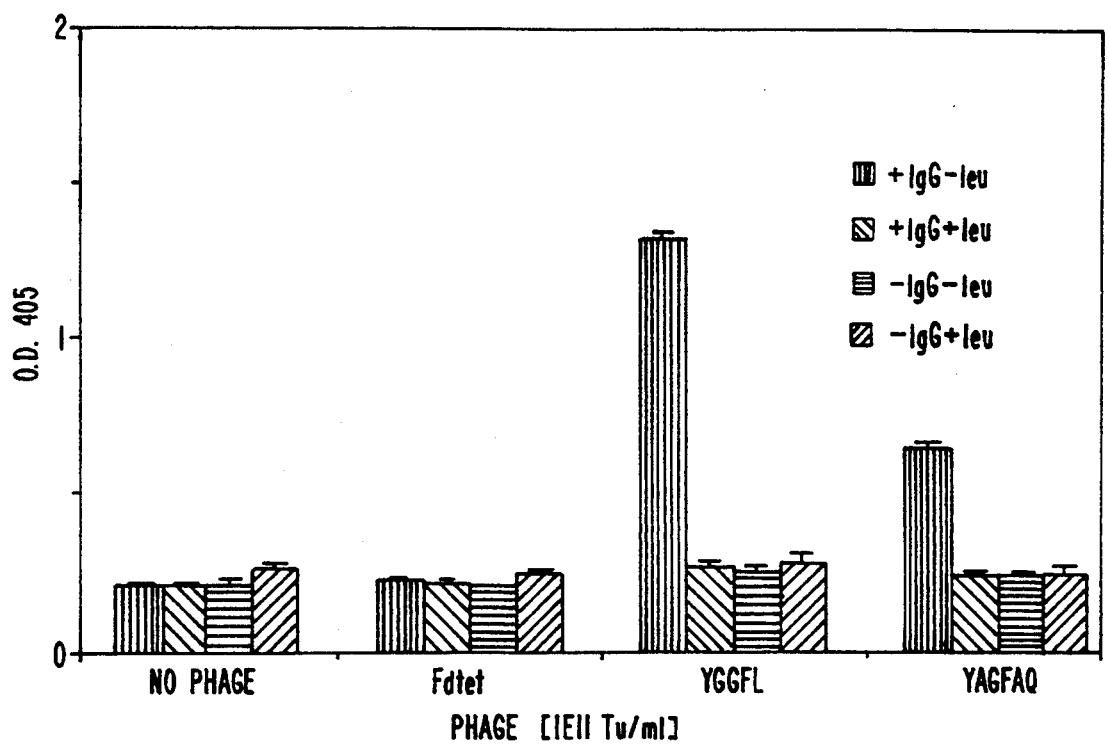
FIG. 5 illustrates the results of phage sandwich ELISAs for YGGFL- and YAGFAQ-phage with biotinylated monoclonal antibody 3E7 IgG (FIG. 5A) or 3E7 Fab fragments (FIG. 5B) immobilized at maximal density on streptavidin coated wells and labeled polyclonal anti-phage antibodies to detect bound phage.
Figure 5B:
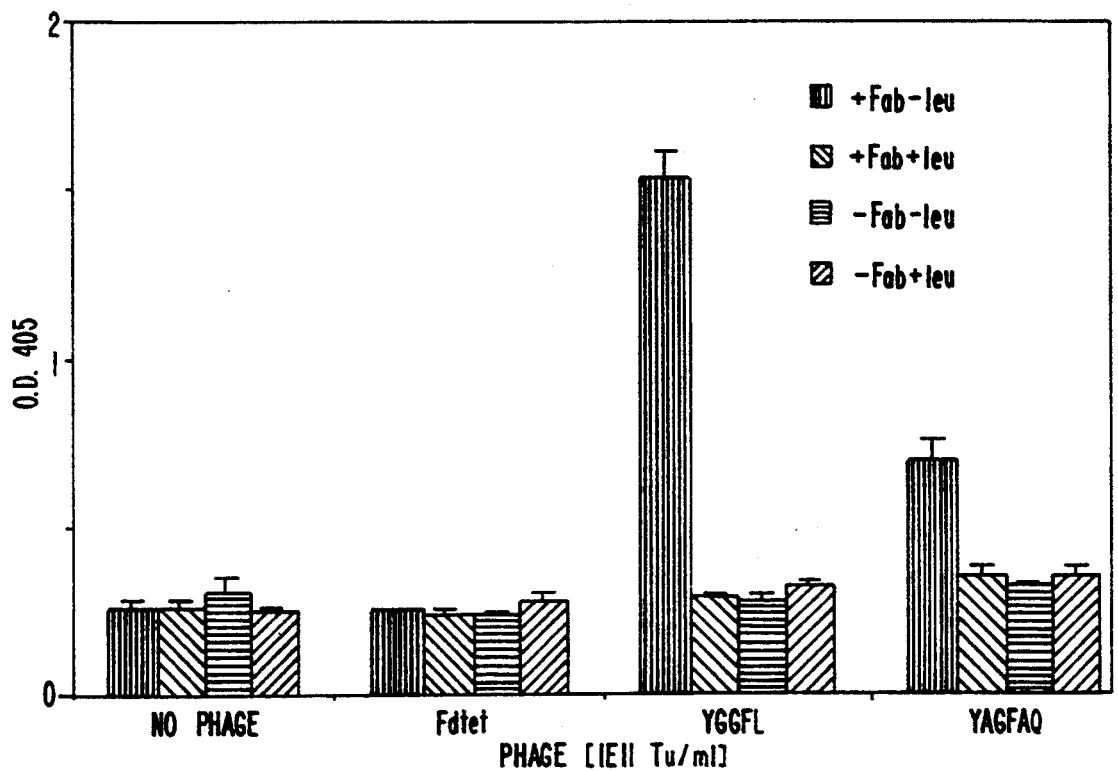

Shown in FIG. 5 are the results of this assay when either biotinylated IgG or Fab was immobilized at maximal density on streptavidin coated wells. Specific binding was detected for both YGGFL- and YAGFAQ-phage; the data indicate that the amount of binding did not differ when IgG and Fab were used. In combination with the data on monovalent dissociation rates of these peptides (see below), this suggests that antibody binding sites for both IgG and Fab are in sufficient proximity to one another to allow simultaneous binding of more than one of the peptides expressed by each phage particle.

The phage sandwich assay can also be used to determine the specificity and competitive nature of the interaction of peptide-bearing phage with immobilized antibody. In practice, an important aspect of the use of peptide on phage libraries is the characterization of individual phage isolates after sequential rounds of the affinity purification. Isolated phage may bind to other components found on an immobilizing surface, or may bind to the protein target at sites other than the active site. Using the phage sandwich assay, the binding of YGGFL- and YAGFAQ-phage was shown to be specific for the antibody and the interaction of the phage with antibody could be blocked by free YGGFL peptide.

Figure 6A:
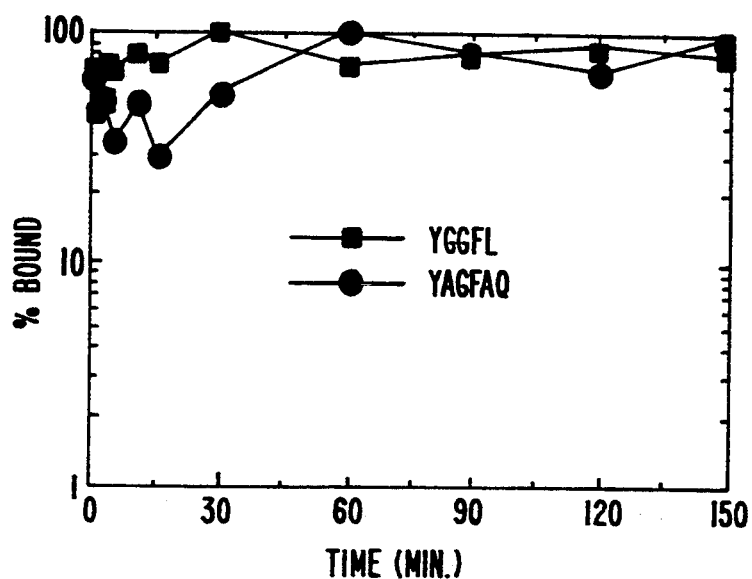
FIG. 6 illustrates the results of phage sandwich ELISAs which compare the effect of 3E7 Fab concentration at 5 nM (FIG. 6A) and 50 pM (FIG. 6B) and wash times (minutes) on recoveries of YGGFL- and YAGFAQ-phage.
Figure 6B:
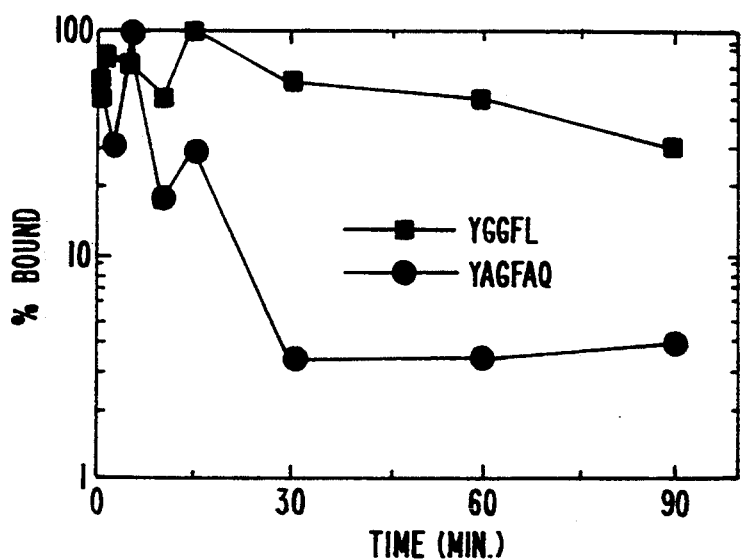

Shown in FIG. 6 are the results of tests on the effect of Fab concentration and wash time on the recoveries of YGGFL- and YAGFAQ-phage. Microtiter wells were coated with streptavidin as described above. $10^{11}$ infectious phage particles bearing the peptides YGGFL or YAGFAQ were incubated overnight at 4° C. with either 50 μl of 5 nM or 50 pM biotinylated Fab. Aliquots were then added to different microtiter wells and incubated for 1 hr. at room temperature. All the wells were washed quickly with TBS/0.05% Tween 20, with the last 200 μl wash being left in the well. At various times thereafter, wells washed quickly with TBS/0.05% Tween and the phage remaining bound were eluted with 0.1M HCl (pH adjusted to 2.2 with glycine) and quantitated by titering as described above.

The results indicate that low Fab concentration (50pM) and dissociation times greater than 30 minutes allowed the selective recovery of phage bearing the higher affinity peptide YGGFL. The use of a high concentration of Fab (5 nM) did not allow the discrimination of phage bearing high and low affinity peptides.

Phage enrichment using a low concentration of biotinylated 3E7 Fab.

A pool of phage previously isolated by three rounds of panning and amplification using 5 nM 3E7 IgG served as starting material for additional affinity purification and amplification using a modification of the previous protocol. Phage ($10^{11}$ infectious particles in 1 ml of TBS) were incubated overnight at 4° C. with 2 ng of biotinylated Fab (50 pM final concentration). The mixture was then exposed to streptavidin-coated plates and bound phage were isolated as described above. Individual phage clones were then isolated and DNA was sequenced as described in Example I above.

Shown in Table 6 are the sequences of peptide inserts of phage that were isolated by 2 rounds of affinity isolation and amplification using 50 pM of biotinylated Fab. A notable difference between the sequences shown in Table 5 and those identified in Example II using three rounds of affinity purification with 50 nM IgG, is the frequency of Phe in the fourth position: 13/19 vs. 10/51

(p<0.05 Fisher Exact Test). Thus, the sequences more highly resemble the known high affinity peptides YGGFL and YGGFM. The sequence YGGFLT was isolated by this procedure and, of the 20 clones that were selected from the final pool of phage, there was only one repeat (the nucleotide sequence was also identical).

TABLE 6

| Seq. ID No. | | Dissociation t1/2 (minutes) | Equilibrium IC50 (nM) |
|---|---|---|---|
| | Control Peptides | | |
| 1 | YGGFL | 18.2 | 6.6 ± 3.5 |
| 2 | YGFWGM | 0.25 | 350 |
| 3 | YAGFAQ | ** | 8300 |
| | Peptides isolated with 50 pM Fab | | |
| 4 | YGAFQG | 18.9 | 27 ± 2.0 |
| 5 | YGGFLT | 17.9 | |
| 6 | YGYWSL | 15.6 | |
| 7 | YGAFMQ | 13.7 | 13 ± 4.9 |
| 8 | YGAFFQ | 13.4 | |
| 9 | YGAFFK | 9.1 | 59 ± 22 |
| 10 | YGFWSN | 7.4 | |
| 11 | YGAFGG | 5.0 | |
| 12 | YGGFGF | 4.7 | 65 ± 18 |
| 13 | YGVFSR | 2.8 | |
| 14 | YGGLSM | 0.96 | |
| 15 | YGTFLN | 0.75 | 470 ± 140 |
| 16 | YGGLVR | 0.50 | |
| 17 | YGSFSL | 0.43 | |
| 18 | YGAWYT | ** | 1600 ± 300 |
| 19 | YGRFFH | ** | |
| 20 | YGGLRH | ** | |
| 21 | YGSFMA | ** | |
| 22 | YGGFSP | ** | |

**indicates that initial binding was not detected

Determination of the dissociation of [$^{125}$I]Fab from fusion phage clones.

Figure 7:
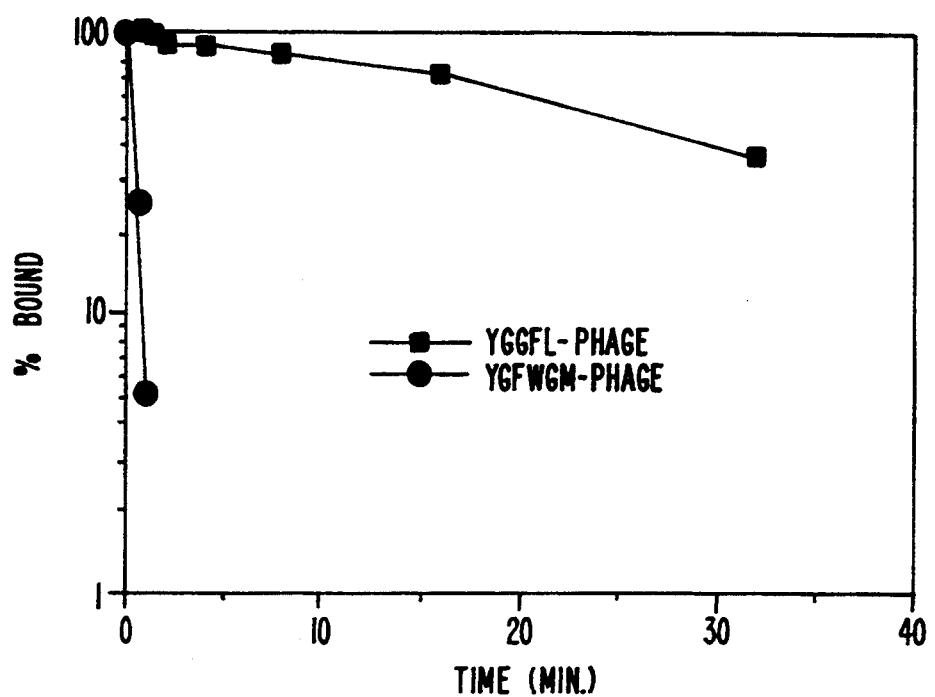
FIG. 7 shows 3E7 Fab dissociation from phage bearing peptides of known affinity, YGGFL and YGFWGM.

An assay employing the anti-phage antisera was developed to determine the rate of dissociation of [$^{125}$I]-Fab from individual phage isolates. Individual fusion phage isolates were amplified in a 5 ml liquid culture of E. coli K91 cells and phage particles were isolated and quantitated as described above. In 1 ml microtiter minitubes, 25 μl of TBS containing approximately 2×10$^9$ infectious phage particles were incubated with 25 ml of TBS/0.1% BSA containing 40,000 cpm of [$^{125}$I]Fab for 10 minutes. Anti-phage antisera (25 μl of 1:1000 dilution in PBS/0.1%BSA) and staph A particles coated with goat anti-mouse IgG (25 μl of Tachisorb diluted eight-fold in TBS/0.1% BSA) were then added. Dissociation was initiated after 2 hours further incubation at 4° C. To prevent binding of unbound [$^{125}$I]Fab, 25 μl of a 400 μM solution of YGGFL in PBS/0.1% BSA was added to all tubes and the amount of phage-bound [$^{125}$I]Fab was determined by automated filtration on glass fiber filters previously treated with 1% BSA. Filter bound radioactivity was determined by gamma counting. Binding was determined in triplicate prior to and 0.5, 1, 2, 4, 8, 16, 32 minutes after the addition of YGGFL peptide. The time corresponding to a 50% reduction of initially bound [$^{125}$I]Fab was determined by linear regression of a semi-logarithmic plot of amount bound vs. time. This assay was calibrated with library phage clones bearing peptides of known affinity (YGGFL, 7 nM and YGFWGM, 350 nM), as shown in FIG. 7.

Shown in Table 6 are the t½ values for the phage clones that were picked from the pool of phage isolated using 5 pM Fab. Several of the clones had t½ values similar to the control phage YGGFL. Specific binding of [$^{125}$I]Fab was not detected for 5 of the 20 clones that were examined.

For a series of related ligands, the rank order of dissociation rates should correlate with the rank order of equilibrium binding constants (Kds). This correlation was confirmed and a quantitative relationship established between dissociation rates and the Kd of the corresponding free peptide. In addition, the affinity requirements for selection using low Fab concentrations were established.

Several peptides corresponding to those phage clones with differing dissociation rates were chemically synthesized and their potencies were determined in a solution competition assay. The t½ values correlated with the IC50 of the corresponding free peptide. Under the conditions of the competition assay (low concentration of tracer, <20% bound tracer, 18 hr. incubation), the IC50 should approximate the Kd. For phage bearing peptides with Kds greater than 500 nM, specific binding was not detected under these monovalent assay conditions.

EXAMPLE IV

Conotoxin Peptide Libraries Having Conserved Disulfide Frameworks.

A conotoxin peptide library is prepared as generally described above, by synthesizing oligonucleotides containing degenerate codons of the NNK (or NNS) motif. Here N is equimolar A,C,G, or T, and K is equimolar G or T (S=G or C). This motif codes for all 20 amino acids at each locus in the hypervariable regions. (Alternatively, the degenerate portion can be assembled by the condensation of 20 activated trinucleotides, one for each amino acid.) The six cysteine codons are preserved to produce the characteristic conotoxin frameworks.

To sample additional diversity in the peptide libraries, the number of residues between the Cys's is varied. This is accomplished as follows:

(1) Five separate oligonucleotide synthesis columns are prepared with the first nucleotide immobilized on resin. (2) The common regions of the 3' end of the oligonucleotides is synthesized (all columns go through the same cycles to produce the cloning site, etc., on this end). Synthesis on all columns is carried out through the first Cys (or CysCys) of the cono-framework. (3) On column 1, two degenerate codons are synthesized; on column 2, three degenerate codons are synthesized, on so on. Each column now has oligonucleotides with either 2,3,4,5, or 6 degenerate codons in the first hypervariable region. (4) One Cys codon is now added to all columns (this is the second Cys of the omega class or the third Cys of the mu class). (5) The resins from all five columns are removed, mixed well, and reallocated among the five columns. Each column now contains oligonucleotides with all five lengths of first hypervariable region. (6) Each column is again put through either 2,3,4,5, or 6 cycles of degenerate codon synthesis as before; and the next Cys codon (or CysCys for omega) is added. (7) The resins are again removed, mixed, and redistributed to the five columns, and the process is repeated through three (for mu) of four (for omega) hypervariable regions. (8) The common sequence on the 5' end of all the oligonucleotides is synthesized, and the oligonucleotides are removed from the resins and purified as usual.

Folding of the peptides to achieve biological activity may be directed by a 40 amino acid conserved "leader peptide" at the N-terminus of the pretoxin molecule. Synthesized as part of a recombinant fusion protein, this leader may enhance the folding of many of the members of the library into the "correct" conotoxin-like framework. Alternatively, allowing the cysteine framework to form in a random manner produces a variety of structures, only some of which mimic the conotoxin framework. This collection provides additional multi-loop structures that add to the diversity of the peptide library.

To minimize the possibility that one conformation would predominate, a gentle reduction of the phage in vitro is employed, followed by mild oxidation to form most of the conformations. Mild reduction/oxidation can be accomplished by treatment with 0.2 to 5 mM DTT followed by extensive dialysis to non-reducing conditions. A regenerable, immobilized lipoic acid column to rapidly pass the peptide-bearing particles over can also be used.

The possibility of promiscuous binding of Cys residues in the peptide binding to other proteins can also be minimized by mild reduction and oxidation, or can be avoided by re-engineering the fusion protein by site-directed mutagenesis to remove the Cys residues.

Peptides with the conotoxin framework can be expressed in several types of libraries as described herein. For example, the peptides can be 1) expressed in an N-terminal library in phage fAFF1; 2) expressed internally, fused to pIII at or near the N-terminus, displacing the degenerate peptides 2 to 10 or more residues from the cleavage point to circumvent processing problems; 3) expressed in a carboxy terminal exposed library (as many of the conotoxins are C-terminally amidated, residues with amino side chains can be added to the C-terminal end of the peptides, or the peptide library, can be amidated in vitro); and 4) the putative 40 residue "folding peptide" can be installed upstream of degenerate peptides displayed in the C-terminally exposed configuration.

This general format for using the secondary framework structure of conotoxins can also be applied to other peptide families with biological activities as a basis for designing and constructing peptide expression/screening libraries in accordance with the present invention.

Although the foregoing invention has been described in some detail by way of illustration and example for purposes of clarity of understanding, it will be apparent that certain changes and modifications may be practiced within the scope of the appended claims.

What is claimed is:

1. A method for obtaining a bacteriophage encoding a substrate cleaved by a preselected proteolytic enzyme, comprising:

(a) transforming host cells with at least $10^6$ different bacteriophage expression vectors, wherein each of said vectors encodes a fusion protein composed of a random peptide fused to a known ligand for a receptor, which known ligand is in turn fused to a coat protein of a filamentous bacteriophage wherein said vectors differ from each other with respect to said random peptides of said fusion protein encoded by said vector and said ligand will not bind said receptor when said ligand is fused to said random peptide;

(b) cultivating said transformed host cells under conditions suitable for expression and assembly of bacteriophage;

(c) incubating said bacteriophage with said preselected proteolytic enzyme under conditions such that a random peptide displayed by said bacteriophage and cleavable by said proteolytic enzyme is cleaved;

(d) contacting said bacteriophage from step (c) to said receptor that binds said known ligand under conditions conducive to specific receptor-ligand binding; and (e) separating receptor-bound bacteriophage from unbound bacteriophage; and thereby obtaining said bacteriophage encoding said substrate for said preselected proteolytic enzyme.

2. A method for obtaining a bacteriophage encoding a substrate cleaved by a preselected proteolytic enzyme, comprising;
   (a) transforming host cells with at least $10^6$ different bacteriophage expression vectors, wherein each of said vectors encodes a fusion protein composed of a known ligand for a receptor fused to a random peptide, which random peptide is in turn fused to a coat protein of a filamentous bacteriophage, and wherein said vectors differ from each other with respect to said random peptide of said fusion protein encoded by said vector;
   (b) cultivating said transformed host cells under conditions suitable for expression and assembly of bacteriophage;
   (c) contacting said bacteriophage from step (b) to said receptor that binds said known ligand under conditions conducive to specific receptor-ligand binding;
   (d) incubating said bacteriophage bound to said receptor with said preselected proteolytic enzyme under conditions such that a random peptide cleavable by said proteolytic enzyme is cleaved;
   (e) separating bacteriophage which are released when said random peptide is cleaved and thereby obtaining said bacteriophage encoding said substrate for said preselected enzyme.

3. A method for identifying a peptide which binds to a preselected receptor and measuring a dissociation rate for the binding of said peptide to said receptor, comprising; p1 (a) transforming host cells with at least $10^6$ different bacteriophage expression vector wherein each of said vectors encodes a fusion protein composed of a peptide fused to a coat protein of a filamentous bacteriophage, and wherein said vectors differ from each other with respect to the peptide of said fusion protein encoded by said vector;
   (b) cultivating said transformed host cells under conditions suitable for expression and assembly of bacteriophage;
   (c) contacting bacteriophage displaying the peptide to the preselected receptor under conditions conducive to specific peptide-receptor binding;
   (d) selecting bacteriophage which bind to the receptor;
   (e) separating bound bacteriophage selected in step (d) into individual isolates;
   (f) binding each isolate separated in step (e) to a labeled monovalent receptor; and
   (g) measuring over time how much receptor binds each isolate in the presence and absence of a known ligand for said receptor to determine a dissociation rate for the binding of said peptide to said receptor.

4. The method of any one of claims 1, 3 or 2, where the receptor is bound to a solid phase and the selected bacteriophage are separated from the culture.

5. The method of any one of claims 1, 3 or 2, wherein the filamentous bacteriophage is f1, fd, or M13.

6. The method of claim 5, wherein the bacteriophage is fd or a derivative thereof.

7. The method of claim 6, wherein the coat protein of the fd bacteriophage is pIII.

8. The method of any one of claims 1, 3 or 2, wherein each of the $10^6$ different bacteriophage expression vectors comprises a series of codons encoding a random collection of amino acids of which said peptide is comprised.

9. The method of claim 8, wherein the codons encoding the collection of amino acids are represented by $(NNK)_x$ or $(NNS)_x$, where N is A, C, G or T, K is G or T, S is G or C, and x is from 5 to 8.

10. The method of any one of claims 1, 3 or 2, wherein the host cells are transformed by electroporation.

11. The method of any one of claims 1, 3 or 2, wherein the oligonucleotide library comprises at least about $10^8$ different expression vectors.

12. The method of any one of claims 1, 3 or 2, wherein the coat protein of the bacteriophage is a preprotein which is processed by the host cell to display the peptide so that an N-terminal amino acid of the fusion protein is an N-terminal amino acid of said peptide.

* * * * *